United States Patent [19]

Theeuwes

[11] 4,160,452
[45] Jul. 10, 1979

[54] OSMOTIC SYSTEM HAVING LAMINATED WALL COMPRISING SEMIPERMEABLE LAMINA AND MICROPOROUS LAMINA

[75] Inventor: Felix Theeuwes, Los Altos, Calif.

[73] Assignee: Alza Corporation, Palo Alto, Calif.

[21] Appl. No.: 785,582

[22] Filed: Apr. 7, 1977

[51] Int. Cl.$^2$ .............................................. A61M 31/00
[52] U.S. Cl. .................................... 128/260; 128/272; 424/19; 424/20; 424/21; 424/22
[58] Field of Search ............... 128/260, 272, 130, 127, 128/213; 424/19–22

[56] References Cited

U.S. PATENT DOCUMENTS

| 3,828,777 | 8/1974 | Ness ...................................... | 128/260 |
| 3,845,770 | 11/1974 | Theeuwes et al. .................... | 128/260 |
| 3,916,899 | 11/1975 | Theeuwes et al. .................... | 128/260 |
| 3,948,254 | 4/1976 | Zaffaroni ............................... | 128/260 |
| 3,961,628 | 6/1976 | Arnold .................................. | 128/260 |
| 3,977,404 | 8/1976 | Theeuwes .............................. | 128/260 |
| 3,981,303 | 9/1976 | Higuchi et al. ....................... | 128/260 |
| 4,008,719 | 2/1977 | Theeuwes et al. .................... | 128/260 |
| 4,014,334 | 3/1977 | Theeuwes et al. .................... | 128/260 |
| 4,036,227 | 7/1977 | Zaffaroni et al. ..................... | 128/260 |

*Primary Examiner*—Benjamin R. Padgett
*Assistant Examiner*—T. S. Gron
*Attorney, Agent, or Firm*—Paul L. Sabatine; Thomas E. Ciotti; Edward L. Mandell

[57] ABSTRACT

An osmotic therapeutic system for delivering a beneficial drug is disclosed. The system comprises a drug delivery module which module comprises a rate controlling laminated wall surrounding a reservoir and has a portal for delivering drug from the system. The laminated wall comprises a semipermeable lamina in laminar arrangement with a microporous lamina to provide a wall that is permeable to an external fluid, impermeable to drug and maintains its integrity during the delivery of drug. The reservoir contains a drug, or a mixture of drug and solute which drug or solute is soluble in the fluid and exhibits an osmotic pressure gradient across the wall against the fluid. In operation, drug is released from the system by fluid being imbibed through the wall into the reservoir at a rate determined by the permeability of the wall and the osmotic pressure gradient across the wall thereby producing a solution of drug, or a solution of solute containing drug which solution is released through the portal at a controlled rate over a prolonged period of time.

14 Claims, 13 Drawing Figures

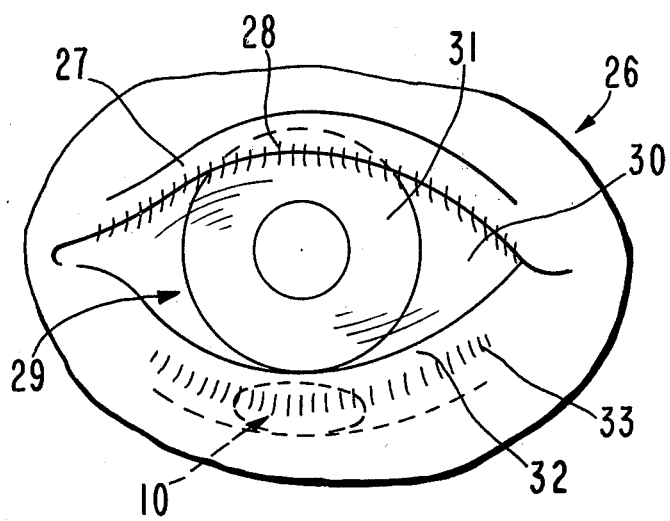
FIG. 5
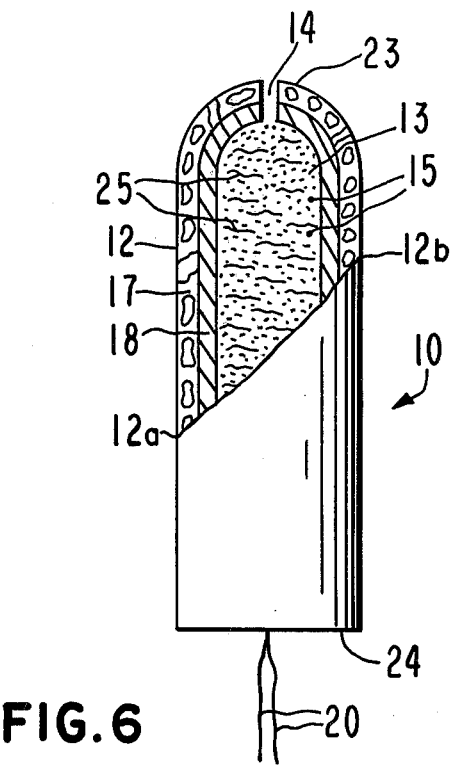
FIG. 6
FIG. 7
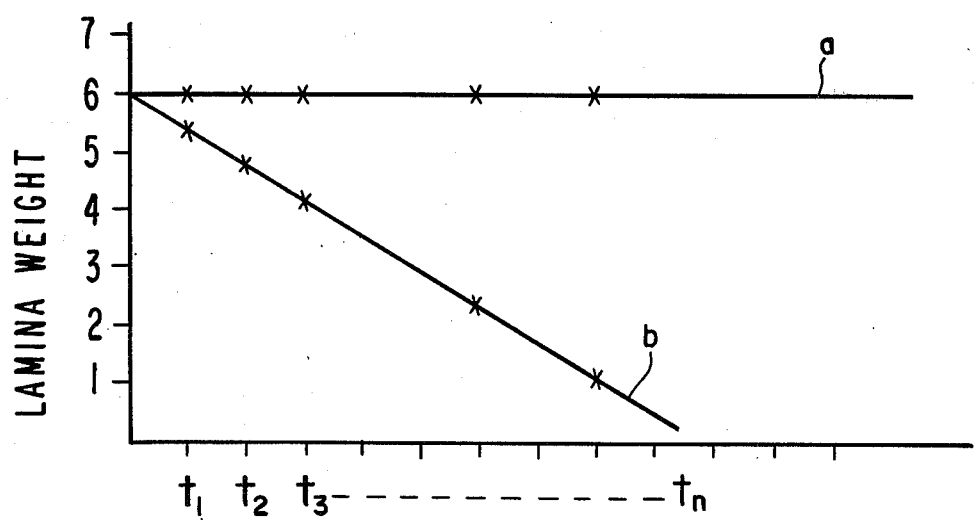

FIG. 8
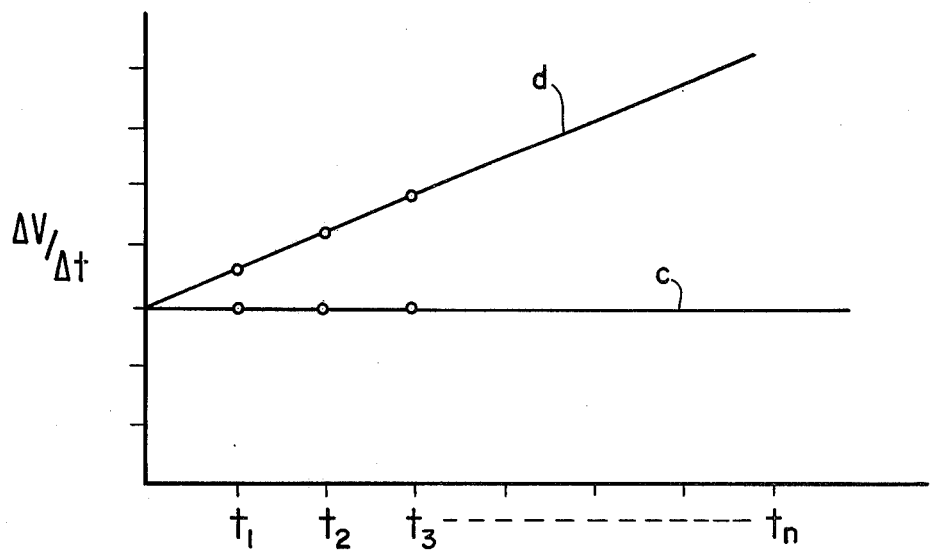
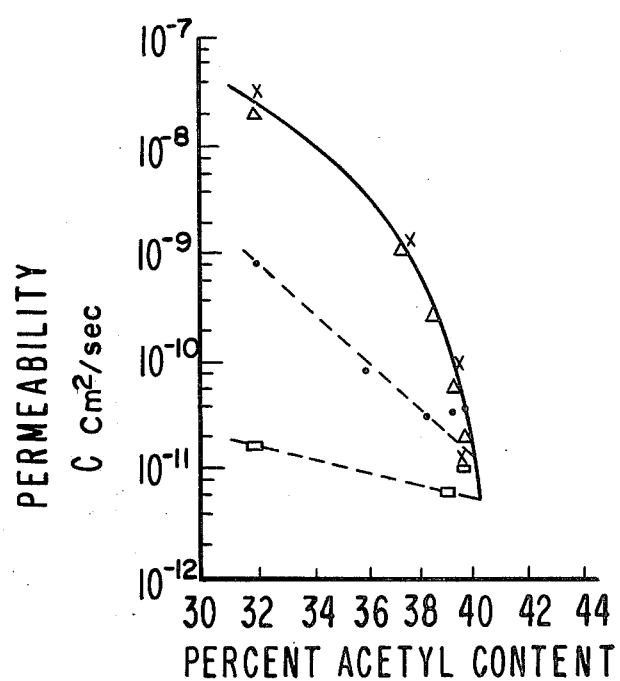
FIG. 9

OSMOTIC SYSTEM HAVING LAMINATED WALL COMPRISING SEMIPERMEABLE LAMINA AND MICROPOROUS LAMINA

FIELD OF THE INVENTION

This invention pertains to a therapeutic osmotic system that is a controlled dosage form. The therapeutic osmotic system provides preprogrammed, unattended delivery of drug at a rate, and for a time period, established to meet a specific therapeutic need. The system is manufactured in the form of an osmotic device for delivering drug to a selected drug receptor site.

BACKGROUND OF THE INVENTION

Osmotic therapeutic systems manufactured in the form of osmotic devices for the precision administration of drugs with control of delivery patterns and with extended operational delivery times are known in U.S. Pat. Nos. 3,845,770 and 3,916,899. The systems disclosed in these patents are made of a single layer wall that surrounds a reservoir containing a drug. The wall is permeable to the passage of an external fluid, impermeable to the passage of drug, and it has a portal for delivering drug from the system. The systems disclosed in these patents are extraordinarily effective for delivering a drug that is soluble in the fluid and exhibits an osmotic pressure gradient across the wall against the fluid, and also for delivering a drug that has limited solubility in the fluid and is mixed with an osmotically effective compound that is soluble in the fluid and exhibits an osmotic pressure gradient across the wall against the fluid. The systems release drug by fluid being imbibed through the wall into the reservoir at a rate determined by the permeability of the wall and the osmotic pressure gradient across the wall producing a solution of soluble drug, or a solution of soluble compound containing drug which solution in either operation is dispensed at a controlled rate over a prolonged period of time. While the above systems represent an outstanding and pioneer advancement in the osmotic art, and while they are useful for dispensing innumerable drugs to the environment of use, it has now been found these osmotic systems can have a unique laminated wall that unexpectedly improves the usefulness and the integrity of the systems.

That is, the systems of this invention comprise a unique laminated wall having a thin lamina formed of a material possessing a given set of properties in laminar arrangement with a supporting, preferably thicker lamina possessing a different set of properties. The system embracing a laminated structure made according to the present invention can have properties such as permeability to external fluids, impermeability to drugs and solutes, and physical and chemical integrity be selected independently, and also have the mode and manner of drug release be made programmable based on the laminae comprising the structured, laminated wall. For example, the wall can comprise a laminae consisting of a thin to very thin lamina facing the environment and a thicker supporting lamina facing the reservoir with each possessing different properties. The lamina facing the environment can be made of a semipermeable material permeable to fluid, impermeable to drug, inert in the presence of drug, and by being thin to very thin in the semipermeable lamina allows an increase in the delivery rate. The lamina facing the reservoir can be made of a microporous material selected to exhibit low to zero resistance to the passage of fluid and drug compared to the semipermeable lamina, which microporous lamina provides structural support for the semipermeable lamina and does not interact with drug and fluid. The structure of the laminated wall allows the use of more inert, polymeric lamina materials which are usually less permeable. The invention's use of a thin rate controlling semipermeable lamina assures that a sufficiently high rate can be maintained for the system. The therapeutic systems made available by this invention and embodying the unique laminated wall thereby functions according to a pre-selected built-in optimal program of drug presentation.

OBJECTS OF THE INVENTION

Accordingly, it is an immediate object of this invention to provide an osmotic therapeutic system for the controlled delivery of a drug to a biological drug receptor site over a prolonged period of time which system is an improvement over the osmotic systems known to the prior art.

Another object of the invention is to provide an osmotic system comprising a laminated wall formed of at least two laminae each made of a different material which materials maintain their physical and chemical integrity during the controlled dispensing of drug over a prolonged period of time.

Yet another object of the invention is to provide an osmotic system comprising a laminated wall comprising a semipermeable lamina and a microporous lamina which laminae are nonerodible and inert during the dispensing of drug.

Still a further object of the invention is to provide an osmotic system having a wide spectrum of laminated walls in which properties such as fluid transmission rates and resistance to attack by the drug may be independently controlled and regulated to a particular application and environment of use.

Yet still another object of the invention is to provide an osmotic system having a laminated wall that has a programmable flux rate to fluids, a high degree of exclusion towards drugs and a resistance to hydrolysis over a wide pH range in the presence of drug and biological fluids.

Yet still another object of the invention is to provide an osmotic system for administering drug where the dose administered contains the intended quantity and is administered at a useful rate to ensure the required onset, intensity and duration of biological response.

Still another object of the invention is to provide an osmotic system for administering a drug wherein the drug is administered as a solution eliminating in vivo dissolution as a controlling mechanism, thereby providing the drug in the most readily available form for absorption by the biological host.

Still another object of the invention is to provide an osmotic system having a laminated wall comprising laminae of different thickness which make the system programmable and versatile, and allows a wider control over the rate drug is released to a drug receptor site.

Other objects, features and advantages of the invention will be more apparent to those skilled in the art from the following detailed specification, taken in conjunction with the drawings and the accompanying claims.

STATEMENT OF THE INVENTION

This invention concerns an osmotic system for dispensing a drug. The system comprises a laminated wall surrounding a reservoir and has a portal for dispensing drug. The compartment contains a drug that is soluble in an external fluid and exhibits an osmotic pressure gradient across the wall against the fluid, or the reservoir contains a mixture of drug having a limited solubility in the fluid and an osmotically effective solute soluble in fluid and exhibits an osmotic pressure gradient across the wall against the fluid. The wall is permeable to fluid, impermeable to drug and solute, and chemically inert towards drug, solute and the environment of use. The wall is formed of a semipermeable lamina laminated to a microporous lamina. Drug is released from the system by fluid being imbibed through the laminated wall into the reservoir at a rate controlled by the wall and the pressure gradient across the wall producing a solution containing agent that is released through the portal at a controlled rate over a prolonged period of time.

BRIEF DESCRIPTION OF THE DRAWINGS

In the drawings, which are not drawn to scale, but are set forth to illustrate various embodiments of the invention, the figures are as follows:

FIG. 5 is a front view of the human eye illustrating an ocular osmotic system positioned in the eye; and, FIG. 6 is a view of an osmotic therapeutic system manufactured for administering drug in the anus with the system seen in opened section for elucidating structural details thereof;

FIG. 7 is a graph comparing a semipermeable lamina, a, that is inert with a semipermeable lamina, b, that slowly loses its integrity in the presence of agent solution;

FIG. 8 is a graph comparing the fluid flux through a semipermeable lamina, c, that maintains its integrity in the presence of fluid with a semipermeable lamina, d, that slowly loses its integrity in the presence of fluid;

FIG. 9 is a graph representing the permeability of a series of semipermeable lamina to a series of osmotic solutes;

In the drawings and specification, like parts in related figures are identified by like numbers. The terms appearing earlier in the specification and in the description of the drawings, as well as embodiments thereof, are further detailed in the disclosure.

DETAILED DESCRIPTION OF THE DRAWINGS

Figure 1:
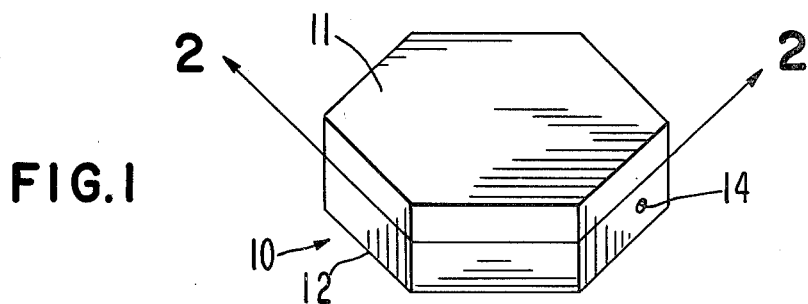
FIG. 1 is a view of an osmotic therapeutic system designed for orally delivering a beneficial agent.
Figure 2:
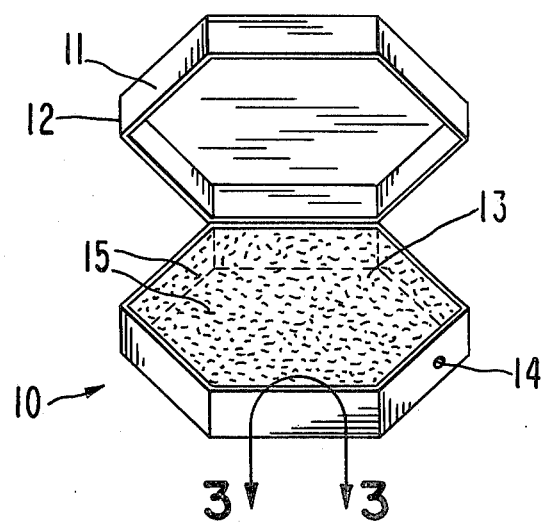
FIG. 2 is a view of the osmotic system of FIG. 1 in opened section through 2—2 illustrating the reservoir of the system.
Figure 3:
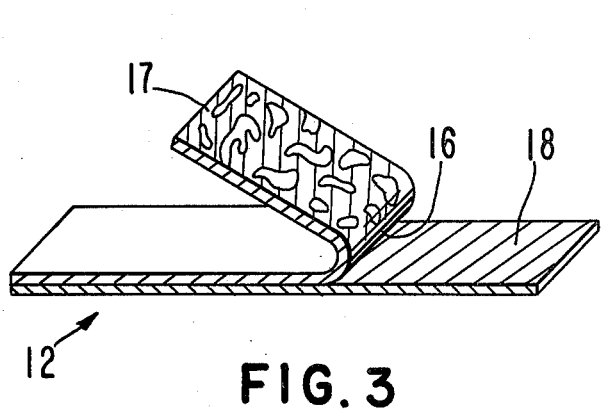
FIG. 3 is a view of a section through 3—3 of the laminated wall of the osmotic system of FIG. 2 illustrating the laminated wall of the system.

Turning now to the drawings in detail, which are examples of various osmotic systems of the invention, and which examples are not to be construed as limiting, one embodiment of an osmotic system is indicated in FIG. 1, 2 and 3 considered together by the numeral 10. In FIGS. 1, 2 and 3 an osmotic system 10 made in the form of an oral, osmotic therapeutic system is comprised of a body 11 having a laminated wall 12 that surrounds a reservoir 13, or compartment, seen in FIG. 2 in opened section through 2—2 of FIG. 1. System 10 has a portal 14, or passageway, in laminated wall 12 that extends through 12 and communicates with reservoir 13 and the exterior of system 10. Reservoir 13, as seen in FIG. 2, is a means for containing a beneficial agent, identified by dot 15, preferably a drug, that is soluble in an external fluid and exhibits an osmotic pressure gradient across 12 against an external fluid, or reservoir 13 optionally contains a mixture of agent 15 having limited solubility in the fluid along with an osmotically effective solute, not seen in FIG. 2, that is soluble in the fluid and exhibits an osmotic pressure gradient across wall 12. Reservoir 13 optionally contains a non-toxic dye for identifying agent 15 and for making release of agent 15 visible to the unaided eye.

Laminated wall 12, as seen in FIG. 3, represents a section through 3—3 removed from wall 12 of system 10 of FIG. 2. Laminated wall 12 is separated at 16 for illustrating the laminae forming the structure of wall 12. Wall 12 comprises a lamina 17 formed of a microporous material and a lamina 18 formed of a semipermeable material. In one operative embodiment, lamina 17 is the interior lamina of wall 12 facing reservoir 13 with lamina 17 functioning as a support or rigid structure for lamina 18. Lamina 17 exhibits low to zero resistance to the passage of fluid and it is substantially free of drug membrane interaction. In the just-described embodiment, lamina 18 is the exterior lamina of wall 12 facing the environment and it is distant from reservoir 13. Lamina 18 is a rate controlling lamina of wall 12 which lamina 18 is permeable to the passage of fluid, impermeable to the passage of agent, drug and solute, it maintains its physical and chemical integrity in the environment of use, and it is more particularly substantially non-erodible and inert in the environment.

In another operative embodiment laminated wall 12 can be manufactured with the microporous lamina 17 positioned facing the environment of use distant from reservoir 13. In this embodiment, semipermeable lamina 18 is positioned as the interior lamina facing compartment 13. The physical, chemical and functional characteristics and properties for lamina 17 and lamina 18 in this embodiment are as described above.

Lamina 18 in yet another embodiment is formed of a single semipermeable material, or lamina 18 is a composite comprising at least two semipermeable wall forming materials. The composite semipermeable lamina is (a) permeable to the passage of an external fluid, (b) substantially impermeable to the passage of drug, agents and solute in the reservoir, (c) maintains its physical and chemical integrity in the presence of agent, drug and fluid, (d) is substantially non-erodible and inert, and (e) can be made thin to very thin while simultaneously controlling the permeability to fluid for imbibition by the system. A detailed description of laminae-forming materials, agents and compounds is pesented later in the specification.

In operation, system 10 in one embodiment releases agent or drug 15 contained in reservoir 13 and soluble in the external fluid by fluid being imbibed into reservoir 13 in a tendency towards osmotic equilibrium at a rate controlled by the permeability of laminated wall 12 and the osmotic pressure gradient across wall 12 to continuously dissolve agent 15 which is osmotically pumped from system 10 through passageway 14 at a controlled and continuous rate over a prolonged period of time. System 10, in another embodiment releases agent 15 that has limited solubility in the fluid and is mixed with an osmotically effective compound by fluid being imbibed through wall 12 into reservoir 13 in a tendency towards osmotic equilibrium at a rate controlled by the permeability of wall 12 and the osmotic pressure gradient across wall 12 to continuously dissolve the osmotically effective compound to form a solution containing agent that is released from system 10 through passageway 15 at a controlled and continuous rate over a prolonged period of time.

Osmotic system 10 of FIGS. 1 through 3 can be made into many useful embodiments including the presently preferred embodiment for oral use. The oral system is useful for releasing in the gastrointestinal tract either a locally or systemically acting agent over a prolonged period of time. Osmotic, oral theraputic system 10 can have various conventional shapes and sizes such as round with a diameter of 3/16 inches to ½ inches, or it can be shaped like a capsule having a range of sizes from triple zero to zero, and from 1 to 8.

Figure 4:
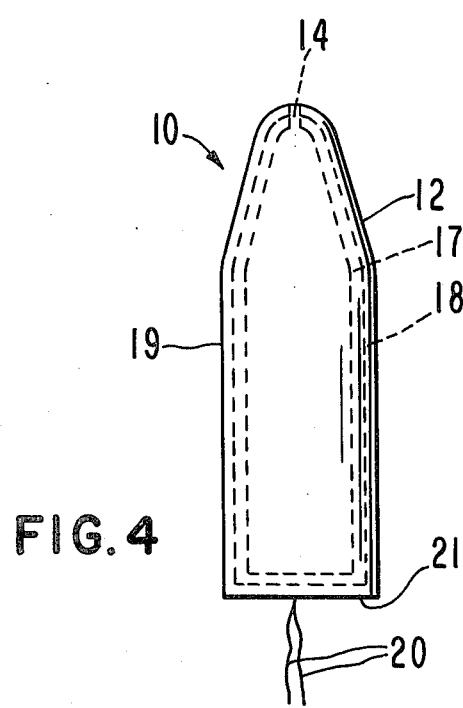
FIG. 4 is a view of an osmotic therapeutic system manufactured for administering drug in the vagina of an animal.

FIG. 4 represents another osmotic therapeutic system 10 manufactured according to the invention for administering drug to a drug receptor. In the illustrated embodiment, system 10 is designed for placement and drug release in the vagina, not shown, of a warm-blooded animal including humans. System 10 has a conically-shaped body 19 with a string 20 attached thereto for removing system 10 from the vaginal vault. System 10 is made with a base 21 big enough to contact, when system 10 is placed in a vagina, the surrounding mucous tissues of the vagina. System 10 comprises a portal 14 and is formed with a laminated wall 12 comprising a microporous lamina 17 and a semipermeable lamina 18. System 10 operates as above described and it is sized, shaped and adapted for placement in the vagina for releasing a drug or fragrance in the vagina.

Referring to FIG. 5, an ocular therapeutic system 10 is seen in eye 26 for administering drug at an osmotically metered dosage rate thereto. In FIG. 5, eye 26 is comprised of an upper eyelid 27 with eyelashes 28, a lower eyelid 32 with eyelashes 33, and an eyeball 29 covered for the greater part by sclera 30 and at its center area by cornea 31. Eyelids 27 and 32 are lined with an epithelial membrane or palpebral conjunctiva, sclera 30 is lined with a bulbar conjunctiva that covers the exposed surface of eyeball 29, and cornea 31 is covered with a transparent epithelial membrane. The portion of the conjunctiva which lines upper eyelid 27 and the underlying portion of the bulbar conjunctiva defines an upper cul-de-sac, while that portion of the palpebral conjunctiva which lines the lower eyelid 35 and the underlying portion of the bulbar conjunctiva defines a lower cul-de-sac. Ocular osmotic system 10, seen in broken lines, is shaped, sized and adapted for placement in the upper or lower cul-de-sac. System 10 is seen in the lower cul-de-sac and it is held in place by the natural pressure of lower eyelid 32. System 10 contains an ophthalmic drug for release to eye 26 at a controlled and continuous rate over a prolonged period of time.

Ocular system 10 can have any geometric shape that fits comfortably in the cul-de-sac. Typical shapes include ellipsoid, bean, banana, circular, rectangular, doughnut, crescent, and half-ring shaped systems. In cross-section, the system can be doubly convex, concavo-convex, rectangular and the like, as the device will in use tend to conform to the shape of the eye. The dimensions of an ocular system can vary widely with the lower limit governed by the amount of drug to be supplied to the eye as well as by the smallest sized system that can be placed into the eye. The upper limit on the size of the system is governed by the space limitation in the eye consistent with confortable retention in the eye. Satisfactory systems generally have a length of 4 to 20 millimeters, a width of 1 to 15 millimeters, and a thickness of 0.1 to 4 millimeters. The ocular system can contain from 0.15 micrograms to 100 milligrams of drug, or more, and it is made from non-erodible and inert materials that are compatible with the eye and its environment.

FIG. 6 illustrates another osmotic therapeutic system 10 designed for administering a locally or systemically acting drug within a body opening, the anal canal, not shown. System 10 is shaped like an obelisk having a lead end 23, a rear end 24, and it is equipped with a string 20 for removing the system from the body. System 10 comprises a laminated wall 12 seen in opened section at 12a to 12b which wall 12 surrounds a reservoir 13 containing drug 15. Drug 15 is soluble in external fluid or it has limited solubility in the fluid and it is optionally mixed with an osmotically effective solute 25 that exhibits an osmotic pressure gradient across wall 12 against external fluid. System 10 has a delivery portal 14 for releasing drug 15 from system 10 to the anal environment. Laminated wall 12 is formed of a pair of laminae 17 and 18 surrounding and forming reservoir 13. In the embodiment illustrated in FIG. 6, lamina 17 is positioned distant from reservoir 13 and lamina 18 is formed of a semipermeable material which lamina 18 is positioned adjacent to reservoir 13. System 10 is sized, shaped and adapted for insertion in the anal canal and it operates in the manner described above.

While FIGS. 1 through 6 are illustrative of various osmotic systems that can be made according to the invention, it is to be understood these systems are not to be construed as limiting, as the systems can take a wide variety of shapes, sizes and forms adapted for delivering agent to different environments of use. For example, the systems include buccal, implant, nose, artificial gland, rectum, cervical, intrauterine, arterial, venous, ear, and like biological environments. The systems also can be adapted for delivering an active agent in streams, aquariums, fields, factories, reservoirs, laboratory facilities, hot houses, transportation means, naval means, air and military means, hospitals, veterinary clinics, nursing homes, chemical reactions and other environments of use.

DETAILED DESCRIPTION OF THE INVENTION

In accordance with the practice of this invention, it has now been found that osmotic system 10 can be successfully manufactured with a laminated wall 12 comprising two different laminae in laminar arrangement that act in concert to form an integral unit wall 12, which maintains its physical and chemical integrity and does not separate into lamina throughout the operative agent release history of osmotic system 10.

Further, in accordance with the practice of the invention, it has been discovered laminated wall 12 can be made in operative embodiment comprising a semipermeable lamina 18 which comprises (a) a single semipermeable lamina forming material, or (b) a semipermeable lamina formed of a blend of lamina forming materials, which semipermeable lamina 18 in either (a) or (b) is in intimate laminar arrangement with a microporous lamina 17 formed of a microporous material. Materials suitable for forming lamina 17 consisting of a single material are generically polymeric materials. The polymeric materials are homopolymers and copolymers and they include materials known as semipermeable, osmosis and reverse osmosis materials. The semipermeable materials are independently selected from semipermeable homopolymers and semipermeable copolymers which generically include polysaccharides comprised of anhydroglucose units. In one embodiment, the polysaccharides are cellulose esters having a degree of substitution, D.S., on the anhydroglucose unit from greater than 0 up to 3 inclusive. By "degree of substitution" as used herein is meant the average number of hydroxyl groups on the anhydroxyl groups on the anhydroglucose unit of the polymer replaced by a substituting group.

Representative materials suitable for forming semipermeable lamina 18 include polymeric cellulose esters and copolymeric cellulose esters such as mono, di and tricellulose acylates. Exemplary polymers include cellulose acetate having a D.S. up to 1 and an acetyl content up to 21%; cellulose diacetate having a D.S. of 1 to 2 and an acetyl content of 21 to 35%; cellulose triacetate having a D.S. of 2 to 3 and an acetyl content of 35 to 44.8%; cellulose propionate having a D.S. of 1.8 and a propionyl content of 38.5%; cellulose acetate propionate having an acetyl content of 1.5 to 7% and a propionyl content of 39 to 42%; cellulose acetate propionate having an acetyl content of 2.5 to 3% and an average combined propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, cellulose triheptylate, cellulose tricaprylate, cellulose trioctanoate, and cellulose tripropionate; cellulose diesters having a lower degree of substitution and prepared by the hydrolysis of the corresponding triester to yield cellulose diacylates having a D.S. of 2.2 to 2.6 such as cellulose disuccinate, cellulose dipalmitate, cellulose dioctanoate, cellulose dicaprylate and cellulose dipentanate and cellulose dipentanate; and esters prepared from acyl anhydrides or acyl acids in an esterification reaction to yield esters containing different acyl groups attached to the same cellulose polymer such as cellulose acetate valerate, cellulose acetate succinate, cellulose propionate succinate, cellulose acetate octanoate, cellulose valerate palmitate, cellulose acetate palmitate and cellulose acetate heptanoate.

Additional semipermeable lamina forming material that can be used for the purpose of the invention include cellulose acetate acetoacetate, cellulose acetate chloroacetate, cellulose acetate furoate, dimethoxyethyl cellulose acetate, cellulose acetate carboxymethoxypropionate, cellulose acetate benzoate, cellulose butyrate naphthylate, cellulose acetate benzoate, methylcellulose acetate, methylcyanoethyl cellulose, cellulose acetate methoxyacetate, cellulose acetate, cellulose acetate ethoxyacetate, cellulose acetate dimethylsulfamate, ethylcellulose dimethylsulfamate, cellulose acetate p-toluene sulfonate, cellulose acetate methylsulfonate, cellulose acetate dipropylsulfamate, cellulose acetate butylsulfonate, cellulose acetate laurate, cellulose sterate, cellulose acetate methylcarbamate, acylated polysaccharides, acylated starches, aromatic nitrogen containing polymeric materials that exhibit permeability to aqueous fluids and substantially no passage to solute, semipermeable membranes made from polymeric epoxides, copolymers of alkylene oxides and alkyl glycidyl ethers, semipermeable polyurethanes, and the like.

Generally, semipermeable materials useful for forming the semipermeable lamina will have a fluid permeability of $10^{-5}$ to $10^{-1}$ (cc mil/cm$^2$ hr atm), expressed per atmosphere (atm) of hydrostatic or osmotic pressure difference across the wall or lamina at the temperature of use while possessing a high degree of impermeability to solute are useful for the purpose of the invention. The polymers described above are known to the art or they can be prepared according to the procedures in *Encyclopedia of Polymer Science and Technology*, Vol. 3, pages 325 to 354, and 459 to 549, published by Interscience Publishers, Inc., New York; in *Handbook of Common Polymers* by Scott, J. R. and Roff, W. J., 1971, published by CRC Press, Cleveland, Ohio; and in U.S. Pat. Nos. 3,133,132; 3,173,876; 3,276,586; 3,541,005; 3,541,006; and 3,546,142.

Further, in accordance with the invention, lamina 18 when formed of a blend of materials consists of, (1) at least one semipermeable lamina forming material permeable to the passage of fluid and other lamina forming compounds blended with at least one or more of the following lamina forming materials, (2) a stabilizing material that imparts physical and chemical integrity to lamina 18, and more particularly gives lamina 18 inertness toward agents, compounds and solutions thereof and to compounds and solutions present in the environment of use, (3) a flux regulator that aids in governing the permeability of fluid through the lamina, (4) a plasticizer that gives flexibility to the lamina, and (5) a dispersant useful for blending the materials into an operative integral composite semipermeable lamina 18. Blends of materials are the invention of Theeuwes and Ayer as described in U.S. patent application Ser. No. 634,859 filed on Nov. 24, 1975 now U.S. Pat. No. 4,077,407 issued Mar. 7, 1978. That application is assigned to the same assignee of this invention.

The stabilizing material homogenously blended with the semipermeable material to form lamina 18 is in a presently preferred embodiment a semipermeable lamina forming material. Suitable stabilizing materials can be selected from the above semipermeable materials for blending with semipermeable lamina 18 forming materials by those skilled in the art by using the procedures described below. These procedures are the lamina weight loss and the osmotic procedure. The procedures use lamina formed with stabilizers and formed without a stabilizer. The lamina weight loss procedure is carried out with lamina that are cast from solution or optionally melt pressed. The lamina are solution cast with a Gardner film-casting knife on a clean glass plate at room temperature with the solution removed by evaporation in an oven at elevated temperatures until the lamina is dry. Next, the lamina is removed from the glass and cut into strips 1 to 10 cm in length, 1 to 10 cm in width and having a thickness of 1 to 10 mils. Then, after all the strips are cut to have the same area and weight, they are placed in a glass container filled with a solution consisting of a known concentration of agent formulated with the fluid of the environment of use. The temperature of the container is made to correspond to the temperature of the environment where an osmotic system formed with the lamina will be placed for releasing agent. At regular time intervals, strips are taken from the solution, rinsed in distilled water, dried in an oven, usually at 50° C. for 24 hours, and weighed. The weight of a single strip repeatedly introduced into the solution, or the weight of many strips consecutively removed at different time intervals are noted and indicated along the ordinate of a graph, and plotted as a function of time indicated along the abscissa, such as $t_1$, $t_2$, $t_3$, etc. as shown in FIG. 7. In FIG. 7, line a represents the results obtained for a lamina that maintains its physical and chemical integrity when exposed to agent solution. That is, the lamina does not lose any weight over time and demonstrates inertness and resistance to erosion in the presence of agent solution. In the same FIG. 7, line b represents a lamina which upon exposure to agent solution, demonstrates a weight loss and is undesirable for making an inert lamina. A stabilizer can be blended into this lamina to enhance its inertness and resistance and substantially prevent weight loss thereby making the lamina useful for fabricating a laminated wall.

In the osmosis procedure, the rate of fluid flow through a lamina is measured and it is performed by exposing the inert lamina to the test environment by using an osmosis cell. The purpose of the procedure is to ascertain, (1) if a given lamina maintains its integrity in the presence of fluid and agent, and (2) if a stabilizer added to the lamina increases its physical and chemical integrity as seen from flux measurements. The measurements are carried out by using a standard osmosis cell and measuring the rate of fluid flow through a lamina made of wall forming material having a known composition and thickness. The flow rate is determined by measuring fluid transport from a first chamber containing a fluid free of agent through a lamina that separates it from a second chamber housing a solution containing a known concentration of agent that exhibits an osmotic gradient across the lamina. Sometimes the chamber contains an osmotically effective compound which is used as an osmotic driving agent. The flow measurement is performed by adding to the first chamber the fluid and then adding to the second chamber, equipped with a stirring bar, the same fluid containing agent, and optionally containing the additional osmotic agents. The first chamber is connected through a conduit to a reservoir containing a supply of fluid and the second chamber is connected to a vertically positioned tube of known diameter and calibrated with indicia that indicates the amount of fluid in the tube. In operation, fluid flows from the first chamber through the lamina into the second chamber by osmosis causing the solution to rise in the tube over time, t, to give volume displacement, $\Delta V$, during a time interval, $\Delta t$. The volume, $\Delta V$, is read on the tube calibrated in cm$^3$, and the time interval, $\Delta t$, is measured with a stopwatch. The value $k_o\pi$ in cm$^3$·mil/cm$^2$·hr for the membrane with permeability, $k_o$, for the agent solution with an osmotic pressure, $\pi$, is calculated from Equation A, and wherein $A_o$ is the area of the lamina, in the diffusion cell, and $h_o$ is the thickness of this lamina.

$$k_o\pi = \frac{\Delta V}{\Delta t} \cdot \frac{h_o}{A_o} \qquad A$$

If the measured value, $k_o\pi$, approximates the calculated value, $k\pi$, the membrane can be used for manufacturing the osmotic device. The data obtained for two different lamina are shown in FIG. 8. In FIG. 8, line c represents a lamina that maintains its integrity in the presence of fluid and agent. That is, since the rate of fluid flow is substantially constant, the lamina does not undergo any substantial change over time, t. Line d shows the fluid flux, $\Delta v/\Delta t$, through a lamina where the rate is continually increasing over time. This change indicates the lamina does not maintain its integrity in the presence of fluid or agent. For those applications where a change in flux is unwanted, a different lamina should be selected for system 10, or a stabilizer added to the lamina to enhance its inertness. The flux through a lamina containing a stabilizer is measured as just described. Other procedures and devices useful for measuring fluid permeability and osmotic flow are disclosed in *J. App. Poly. Sci.*, Vol. 9, pages 1341 to 1362, 1965; and in *Yale J. Biol. Med.*, Vol. 42, pages 139 to 153, 1970.

Additional scientific criterions that can be used by those skilled in the art for selecting a stabilizing material include the following: (a) the material possesses a high degree of substitution, for example, the material has undergone etherification or esterification particularly acylation towards or to completion with the lamina formed containing stabilizers that demonstrate increased resistance to hydrolysis and increased rejection of agent, (b) the stabilizer exhibits a flux decrease to fluid and solute with increasing molecular size of the substituting group, (c) the stabilizer exhibits a flux decrease proportional to the increase in size of the substituent, for example, the decrease occurs as the number of carbon atoms increase in a hydrocarbon moiety such as an alkyl or alkoxy moiety, (d) the stabilizer exhibits increased stability with an increase in the degree of substitution of hydrophobic ether and larger hydrophobic ester groups with an accompanying decrease in the degree of substitution of smaller hydrophilic ester groups, and (e) the stabilizer exhibits a flux decrease as the number of polar, ionic groups bonded to the stabilizer decrease. These principles are exemplified and illustrated in FIG. 9. FIG. 9 is an illustration of the decrease in polymer permeability to solutes such as sodium chloride indicated by X, potassium chloride indicated by $\Delta$, magnesium sulfate indicated by 0, and potassium sulfate indicated by $\square$, with increasing degrees of substitution by ester groups including acetyl moieties. A lower permeability to solute signifies a higher rejection or exclusion of the solute from the polymer network, thereby diminishing the chance for polymer-solute interaction, while increasing the solubility of the polymer. The trends shown in FIG. 9 for the indicated solutes hold for other agents. Generally, the amount of stabilizer used will range from 1 to 90 parts based on 100 parts of semipermeable lamina.

The expressions "flux regulator agent," "flux enhancing agent" and "flux decreasing agent" as used herein means a compound that when added to semipermeable lamina forming material assists in regulating the fluid permeability or liquid flux through the lamina. The agent can be preselected to increase or decrease the liquid flux. Agents that produce a marked increase in permeability to fluid such as water, are often essentially hydrophilic, while those that produce a marked decrease to fluid such as water, are essentially hydrophobic. The flux regulators in some embodiments also can increase the flexibility of the lamina. The flux regulators in one embodiment, are polyhydric alcohols and derivatives thereof, such as polyalkylene glycols of the formula H—(O-alkylene)$_n$—OH wherein the bivalent alkylene radical is straight or branched chain and has from 1 to 10 carbon atoms and n is 1 to 500 or higher. Typical glycols include polyethylene glycols 300, 400, 600, 1500, 1540, 4000, and 6000 of the formula H—(OCH$_2$CH$_2$)$_n$—OH wherein n is respectively 5 to 5.7, 8.2 to 9.1, 12.5 to 13.9, 29 to 36, 29.8 to 37, 68 to 84, and 158 to 204. Other polyglycols include the low molecular weight glycols such as polypropylene, polybutylene and polyamylene.

The flux regulators in another embodiment include poly($\alpha,\omega$)-alkylenediols wherein the alkylene is straight or branched chain of from 2 to 10 carbon atoms such as poly(1,3)-propanediol, poly(1,4)-butanediol, poly(1,5)-pentanediol and poly(1,6)-hexanediol. The diols also include aliphatic diols of the formula HOC$_n$H$_{2n}$OH wherein n is from 2 to 10 and the diols are optionally bonded to a non-terminal carbon atom such as 1,3-butylene glycol, 1,4-pentamethylene glycol, 1,5-hexamethylene glycol and 1,8-decamethylene glycol; and alkylenetriols having 3 to 6 carbon atoms such as glycerine, 1,2,3-butanetriol, 1,2,3-pentanetriol, 1,2,4-hexanetriol and 1,3,6-hexanetriol.

Other flux regulators include esters and polyesters of alkylene glycols of the formula HO—(alkylene-O)$_n$—H wherein the divalent alkylene radical includes the straight chain groups and the isomeric forms thereof having from 2 to 6 carbons and n is 1 to 14. The esters and polyesters are formed by reacting the glycol with either a monobasic or dibasic acid. Exemplary flux regulators are ethylene glycol dipropionate, ethylene glycol butyrate, ethylene glycol diacetate, triethylene glycol diacetate, butylene glycol dipropionate, polyester of ethylene glycol with succinic acid, polyester of diethylene glycol with maleic acid and polyester of triethylene glycol with adipic acid.

Figure 10:
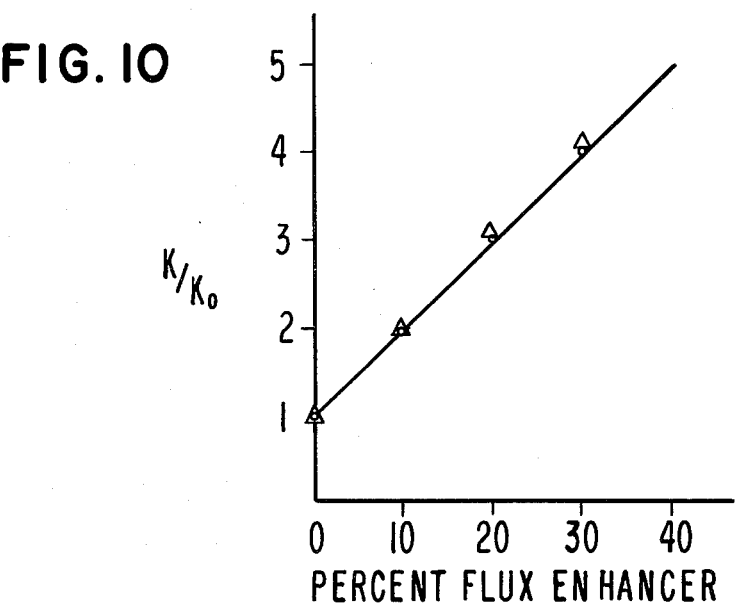
FIG. 10 represents the ratio of the fluid permeability of a semipermeable lamina containing a flux regulator to the fluid permeability of the same semipermeable lamina without flux enhancer.

Suitable flux regulators for compounding with a semipermeable material to increase or decrease its fluid permeability can be selected by blending known amounts of a regulator with the material, casting the blends into a thin lamina, and then measuring the change in permeability towards the fluid found in the environment of use. For example, to two separate batches of lamina forming cellulose acetate having an acetyl content of 32% and 39.8% were added 1, 2 and 3 grams of flux regulator polyethylene glycol having a molecular weight of 400 and the ingredients blended in a high shear blender in the presence of 120 ml of dimethyl formamide to yield six blends. Next, the blends were solvent cast with a Gardner knife and dried in an oven for 7 days at 50° C. The water permeability of the six laminae was measured in the osmosis cell described above and the results recorded in FIG. 10. In FIG. 10, the triangles represent cellulose acetate 32% and the circles represent cellulose acetate 39.8%. Also, as recorded on the ordinate, $k_o$ indicates the water permeability through cellulose acetate 32% free of flux regulator and cellulose acetate 39.8% that did not contain any flux regulator, and k indicates the water permeability through cellulose acetate 32% and cellulose acetate 39.8% where both contained the flux regulator. The positive integers 10, 20, 30 and 40 recorded on the abscissa, indicate the percent of flux regulator in the lamina. Using the above technique, specific flux regulators for blending with specific semipermeable materials to regulate the permeability can be selected for making the desired lamina for making a laminated wall. The amount of flux regulator added to a material generally is an amount sufficient to produce the desired permeability, and it will vary according to the lamina forming material and the flux regulator used to modulate the permeability. Usually, from 0.001 parts up to 40 parts, or higher of flux regulator can be used to achieve the desired results, with a presently preferred range consisting of 0.1 part up to 30 parts of regulator or mixtures thereof for 100 parts of lamina forming material.

Exemplary plasticizers suitable for the present purpose generically include plasticizers that lower the temperature of the second-order phase transition of the lamina forming material or the elastic modulus thereof, increase the workability of the lamina, its flexibility, and its permeability to fluid. Plasticizers operable for the present purpose include both cyclic plasticizers and acyclic plasticizers. Typical plasticizers are those selected from the group consisting of phthalates, phosphates, citrates, adipates, tartrates, sebacates, succinates, glycolates, glycerolates, benzoates, myristates, sulfonamides, and halogenated phenyls.

Exemplary plasticizers further include dialkyl phthalates, dicycloalkyl phthalates, diaryl phthalates and mixed alkyl-aryl phthalates as represented by dimethyl phthalate, dipropyl phthalate, di(2-ethylhexyl)phthalate, di-isopropyl phthalate, diamyl phthalate and dicapryl phthalate; alkyl and aryl phosphates such as tributyl phosphate, trioctyl phosphate, tricresyl phosphate, trioctyl phosphate, tricresyl phosphate and triphenyl phosphate; alkyl citrate and citrate esters such as tributyl citrate, triethyl citrate, and acetyl triethyl citrate; alkyl adipates such as dioctyl adipate, diethyl adipate and di(2-methoxyethyl)adipate; dialkyl tartrates such as diethyl tartrate and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate, glycerol monolactate diacetate, methyl phythayl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate. Other plasticizers include camphor, N-ethyl-(o- and p-toluene) sulfonamide, chlorinated biphenyl, benzophenone, N-cyclohexyl-p-toulene sulfonamide, and substituted epoxides.

Suitable plasticizers can be selected for blending with the lamina forming materials by selecting plasticizers that have a high degree of solvent power for the materials, are compatible with the materials over both the processing and use temperature range, exhibit permanence as seen by a strong tendency to remain in the plasticized lamina, impart flexibility to the lamina, and are non-toxic to animals, humans, avians, fishes and reptiles. Procedures for selecting a plasticizer having the described characteristics are disclosed in the *Encyclopedia of Polymer Science and Technology*, Vol. 10, pages 228 to 306, 1979, published by John Wiley & Sons, Inc., New York. Also, a detailed description pertaining to the measurement of plasticizer properties, including solvent parameters and compatibility, the Hildebrand solubility parameter, the Flory-Huggins interaction parameter, and the cohesive-energy density, CDE, parameter is disclosed in *Plasticization and Plasticizer Processes, Advances in Chemistry Series* 48, Chapter 1, pages 1 to 26, 1965, published by the American Chemical Society, Washington, D.C. The amount of plasticizer added generally is an amount sufficient to produce the desired lamina and it will vary according to the plasticizer and the materials. Usually about 0.001 part up to 20 parts, or higher, of the plasticizer can be used for 100 parts of lamina forming material with a presently preferred range of 0.1 part to 15 parts of plasticizer, or mixtures thereof for 100 parts of lamina forming materials.

Dispersants useful for the present purpose are those dispersants when added to a lamina forming material and other materials aid in producing an integral composite that is useful for making the operative laminated wall of a system. The dispersants act by regulating the surface energy of materials to improve their blending into the composite. This latter material is used for manufacturing devices that maintain their integrity in the environment of use during the agent release period. Generally, the dispersants are amphipathic molecules comprised of a hydrophobic part and a hydrophilic part. The dispersants can be anionic, cationic, nonionic or amphoteric and they include anionics such as sulfated esters, amides, alcohols, ethers and carboxylic acids; sulfonated aromatic hydrocarbons, aliphatic hydrocarbons, esters and ethers; acylated amino acids and peptides; and metal alkyl phosphates; cationic dispersants such as primary, secondary, tertiary and quaternary alkylammonium salts; acylated polyamines; and salts of heterocyclic amines, arylammonium dispersants such as esters of polyhydric alcohols; alkoxylated amines; polyoxyalkylene; esters and ethers of polyoxyalkylene glycols; alkanolamine fatty acid condensates; tertiary acetylamic glycols; and dialkyl polyoxyalkylene phosphates; and ampholytics such as betamines; and amino acids.

Typical dispersants include polyoxyethylenated glycerol ricinoleate polyoxyethylenated castor oil having from 9 to 52 moles of ethylene oxide; glycerol mannitan laurate, and glycerol(sorbitan oleates, stearates or laurates); polyoxyethylenated sorbitan laurate, palmitate, stearate, oleate or hexaolate having from 5 to 20 moles of ethylene oxide; mono-, di- and poly-ethylene glycol stearates, laurates, oleates, myristates, behenates or ricinoleates; propylene glycol carboxylic acid esters; sorbitan laurate, palmitate, oleate, and stearate; polyoxyethylenated octyl, nonyl, decyl, and dodecylphenols having 1 to 100 moles of ethylene oxide; polyoxyethylenated nonyl, lauryl, decyl, cetyl, oleyl and stearyl alcohols having from 3 to 50 moles of ethylene oxide; polyoxypropylene glycols having from 3 to 300 moles of ethylene oxide; sodium salt of sulfated propyl oleate; sodium di(heptyl)sulfosuccinate; potassium xylenesulfonate; 1:1 myristic acid diethanolamide; N-coco-$\beta$-aminopropionic acid; bis-(2-hydroxyethyl)tallowamine oxide; (diisobutyl-phenoxyethoxyethyl)dimethylbenzylammonium halide; N,N'-polyoxypropylenated ethylendiamine having a molecular weight from 500 to 3000; tetralkylammonium salts with up to 26 carbon atoms in the cation; sodium or potassium salt of polypeptide cocoanut, oleic or undercylenic acid condensate; metal salts of N-acylated short chain aminosulfonic acids; soybean phosphatides; and sulfobetaine.

Suitable dispersants can be selected from the above and from other dispersants for blending with laminae forming materials by using the dispersant's hydrophile-lipophile balance number, HLB. This number represents the proportion between the weight percentages of hydrophilic and lipophilic groups in a dispersant. In use, the number indicates the behavior of the dispersant, that is, the higher the number the more hydrophilic the dispersant and the lower the number the more lipophilic the dispersant. The required HLB number for blending lamina forming materials is determined by selecting a dispersant with a known number, blending it with the materials and observing the results. A homogenous composite is formed with the correct number; while a heterogenous mixture indicates a different number is needed. This new number can be selected by using the prior number as a guide. The HLB number is known to the art for many dispersants, and they can be experimentally determined according to the procedure in *J. Soc. Cosmetic Chem.*, Vol. 1, pages 311 to 326, 1949, or it can be calculated by using the procedure in *J. Soc. Cosmetic Chem.*, Vol. 5, pages 249 to 256, 1954, and in *Am. Perfumer Essent. Oil Rev.*, Vol. 65, pages 26 to 29, 1955. Typical HLB numbers are set forth in Table 1. Generally a number of 10 or less indicates lipophilic behavior and 10 or more indicates hydrophilic behavior. Also, HLB numbers are algebraically additive. Thus, by using a low number with a high number, blends of dispersants can be prepared having numbers intermediate between the two numbers. The amount of dispersant needed is an amount that when blended with lamina forming materials will form the desired composite; this will vary according to the particular dispersant and materials that are blended to form the lamina. Generally the amount of dispersant will range from about 0.001 parts up to 15 parts, or higher, for 100 parts of lamina forming material with a presently preferred range of 0.1 part to 10 parts of dispersant or mixtures thereof, for 100 parts of lamina forming material.

TABLE 1

| DISPERSANT | HLB NUMBER |
| --- | --- |
| Sorbitan trioleate | 1.8 |
| Polyoxyethylene sorbitol beeswax | 2.0 |
| Sorbitan tristearate | 2.1 |
| Polyoxyethylene sorbitol hexastearate | 2.6 |
| Ethylene glycol fatty acid ester | 2.7 |
| Propylene glycol fatty acid ester | 3.4 |
| Propylene glycol monostearate | 3.4 |
| Ethylene glycol fatty acid ester | 3.6 |
| Glycerol monostearate | 3.8 |
| Sorbitan monooleate | 4.3 |
| Propylene glycol monolaurate | 4.5 |
| Diethylene glycol fatty acid ester | 5.0 |
| Sorbitan monopalmitate | 6.7 |
| Polyoxyethylene dioleate | 7.5 |
| Polyoxypropylene mannitol dioleate | 8.0 |
| Sorbitan monolaurate | 8.6 |
| Polyoxyethylene lauryl ether | 9.5 |
| Polyoxyethylene sorbitan monolaurate | 10.0 |
| Polyoxyethylene lanolin derivative | 11.0 |
| Polyoxyethylene glycol 400 monooleate | 11.4 |
| Triethanolamine oleate | 12.0 |
| Polyoxyethylene nonyl phenol | 13.0 |
| Polyoxyethylene sorbitan monolaurate | 13.3 |
| Polyoxyethylene sorbitol lanolin | 14.0 |

TABLE 1-continued

| DISPERSANT | HLB NUMBER |
| --- | --- |
| Polyoxyethylene stearyl alcohol | 15.3 |
| Polyoxyethylene 20 cetyl ether | 15.7 |
| Polyoxyethylene 40 stearate | 16.9 |
| Polyoxyethylene monostearate | 17.9 |
| Sodium oleate | 18.0 |
| Potassium oleate | 20.0 |

Microporous materials suitable for making lamina 17 of system 10 are those materials that can form a microporous lamina which lamina 17 can be laminated to semipermeable lamina 18 to form laminated wall 12. The microporous materials suitable for forming the lamina are essentially inert, they maintain their physical and chemical integrity during the period of agent release and they can be generically described as having a sponge-like appearance that provides a supporting structure for semipermeable lamina 18 and also provides a supporting structure for microscopic-sized interconnected pores or voids. The materials can be isotropic wherein the structure is homogenous throughout a cross-sectional area, or they can be anisotropic wherein the structure is non-homogenous throughout a cross-sectional area. The pores can be continuous pores that have an opening on both faces of a microporous lamina, pores interconnected through tortuous paths of regular and irregular shapes including curved, curved-linear, randomly oriented continuous pores, hindered connected pores and other porous paths discernible by microscopic examination. Generally microporous lamina are defined by the pore size, the number of pores, the tortuosity of the microporous path and the porosity which relates to the size and the number of pores. The pore size of a microporous lamina is easily ascertained by measuring the observed pore diameter at the surface of the material under the electron microscope. Generally, materials possessing from 5% to 95% pores and having a pore size of from 10 angstroms to 100 microns can be used for making lamina 18. The pore size and other parameters characterizing the microporous structure also can be obtained from flow measurements, where a liquid flux, J, is produced by a pressure difference $\Delta P$, across a lamina. The liquid flux through a lamina with pores of uniform radius extended through the membrane and perpendicular to its surface with area A given by the relation (1):

$$J = \frac{N\pi r^4 \Delta P}{8\eta \Delta x} \quad (1)$$

wherein J is the volume transported per unit time and lamina area containing N number of pores of radius, r, $\eta$ is the viscosity of the liquid, and $\Delta P$ is the pressure difference across the lamina with thickness $\Delta x$. For this type of lamina, the number of pores N can be calculated from relation (2), wherein $\epsilon$ is the porosity defined as the ratio of void volume to total volume of the lamina:

$$N = \epsilon \times \frac{A}{\pi r^2} \quad (2)$$

The pore radius then is calculated from relation (3):

$$r = \left( 8\eta \frac{J \cdot \Delta x \cdot \tau}{\Delta P \cdot \epsilon} \right)^{\frac{1}{2}} \quad (3)$$

wherein J is the volume flux through the lamina per unit area produced by the pressure difference $\Delta P$ across the lamina, $\beta$, $\epsilon$ and $\Delta x$ have the meaning defined above and $\tau$ is the tortuosity defined as the ratio of the diffusional path length in the lamina to the lamina thickness. Relations of the above type are discussed in *Transport Phenomena In Membranes*, by Lakshminatayanaiah, N., Chapter 6, 1969, published by Academic Press, Inc., New York.

As discussed in this reference on page 336, in Table 6.13, the porosity of the lamina having pore radii r can be expressed relative to the size of the transported molecule having a radius a, and as the ratio of molecular radius to pore size radius a/r decreases, the lamina becomes porous with respect to this molecule. That is, when the ratio a/r is less than 0.3, the lamina becomes substantially microporous as expressed by the osmotic reflection coefficient $\sigma$ which decreases below 0.05. Microporous lamina with a reflection coefficient $\sigma$ in the range of less than 1, usually from 0 to 0.5, and preferably less than 0.1 with respect to the active agent are suitable for fabricating the system. The reflection coefficient is determined by shaping the material in the form of a lamina and carrying out water flux measurements as a function of hydrostatic pressure difference and as a function of the osmotic pressure difference caused by the active agent. The osmotic pressure difference creates an osmotic volume flux, the hydrostatic pressure difference creates a hydrostatic volume flux, and the reflection coefficient is expressed by relation 4:

$$\sigma = \frac{\text{hydrostatic pressure difference} \times \text{osmotic volume flux}}{\text{osmotic pressure difference} \times \text{hydrostatic volume flux}} \quad (4)$$

Properties of microporous materials are described in *Science*, Vol. 170, pages 1302 to 1305, 1970; *Nature*, Vol. 214, page 285, 1967; *Polymer Engineering and Science*, Vol. 11, pages 284 to 288, 1971; U.S. Pat. Nos. 3,567,809 and 3,751,536; and in *Industrial Processing With Membranes*, by Lacey, R. E., and Loeb, Sidney, pages 131 to 134, 1972, published by Wiley, Interscience, New York.

Microporous materials are commercially available and they can be made by art-known methods. The materials can be made by etched nuclear tracking, by cooling a solution of flowable polymer below the freezing point whereby solvent evaporates from the solution in the form of crystals dispersed in the polymer and then curing the polymer followed by removing the solvent crystals, by cold or hot stretching at low or high temperatures until pores are formed, by leaching from a polymer a soluble component by an appropriate solvent, by ion exchange reaction, and by polyelectrolyte processes. Processes for preparing microporous materials are described in *Synthetic Polymer Membranes*, by R. E. Kesting, Chapters 4 and 5, 1971, published by McGraw Hill, Inc.; *Chemical Reviews*, Ultrafiltration, Vol. 18, pages 373 to 455, 1934; *Polymer Eng. and Sci.*, Vol. 11, No. 4, pages 284 to 288, 1971; *J. Appl. Poly. Sci.*, Vol. 15, pages 811 to 829, 1971; and in U.S. Pat. Nos. 3,565,259; 3,615,024; 3,751,536; 3,801,692; 3,852,244; and 3,849,528.

Microporous materials useful for making the lamina include microporous polycarbonates comprised of linear polyesters of carbonic acid in which carbonate groups recur in the polymer chain, microporous materials prepared by the phosgenation of a dihydroxyl aromatic such as bisphenol a, microporous poly(vinylchloride), microporous polyamides such as polyhexamethylene adipamide, microporous modacrylic copolymers including those formed from poly(vinylchloride) 60% and acrylonitrite, styrene-acrylic and its copolymers, porous polysulfones characterized by diphenylene sulfone groups in a linear chain thereof, halogenated poly(vinylidene), polychloroethers, acetal polymers, polyesters prepared by esterification of a dicarboxylic acid or anhydride with an alkylene polyol, poly(alkylenesulfides), phenolic polyesters, microporous poly(saccharides), microporous poly(saccharides) having substituted and unsubstituted anhydroglucose units and preferably exhibiting a decrease permeability to the passage of water and biological fluids than semipermeable lamina 18, asymmetric porous polymers, cross-linked olefin polymers, hydrophobic or hydrophilic microporous homopolymers, copolymers or interpolymers having a reduced bulk density, and materials described in U.S. Pat. Nos. 3,595,752; 3,643,178; 3,654,066; 3,709,774; 3,718,532; 3,803,061; 3,852,224; 3,853,601; and 3,852,388, in British Pat. No. 1,126,849, and in *Chem. Abst.*, Vol. 71 4274F, 22572F, 22573F, 1969.

Additional microporous materials include poly(urethanes), cross-linked, chain-extended poly(urethanes), microporous poly(urethanes) in U.S. Pat. No. 3,524,753, poly(imides), poly(benzimidazoles), collodion (cellulose nitrate with 11% nitrogen), regenerated proteins, semisolid cross-linked poly(vinylpyrrolidone), microporous materials prepared by diffusion of multivalent cations into polyelectrolyte sols as in U.S. Pat. No. 3,565,259, anisotropic permeable microporous materials of ionically associated polyelectrolytes, porous polymers formed by the coprecipitation of a polycation and a polyanion as described in U.S. Pat. Nos. 3,276,589, 3,541,005, 3,541,006, and 3,546,142, derivatives of poly(styrene) such as poly(sodium styrenesulfonate) and poly(vinyl benzyltrimethyl-ammonium chloride), the microporous materials disclosed in U.S. Pat. No. 3,615,024 and U.S. Pat. Nos. 3,646,178 and 3,852,224.

The expression "portal" as used herein comprises means and methods suitable for releasing the agent from the system. The expression includes passageway, an aperture, orifice or bore through the laminated wall formed by mechanical procedures or by eroding an erodible element, such as a gelatin plug, in the environment of use. A detailed description of osmotic portals or passageways in the maximum and minimum dimensions for same are disclosed in U.S. Pat. Nos. 3,845,770 and 3,916,899.

The osmotically effective compounds that can be used for the purpose of the invention include inorganic and organic compounds that exhibit an osmotic pressure gradient against an external fluid across the laminated wall of the system. The compounds are used mixed with an agent that has limited solubility in the external fluid with the compounds forming a saturated solution containing agent that is osmotically delivered from the system. The phrase "limited solubility" as used herein means the agent has a solubility of about less than 1% by weight in the external fluid. The compounds are used by homogeneously or heterogeneously mixing the compound or a mixture of compounds with an agent, either before they are charged into the reservoir, or by self-mixing after they are charged into the reservoir. In operation, these compounds attract fluid into the system producing a solution of compound which is delivered from the system concomitantly transporting undissolved and dissolved agent to the exterior of the system. Osmotically effective compounds useful for the present purpose include magnesium sulfate, magnesium chloride, sodium chloride, lithium chloride, potassium sulfate, sodium carbonate, sodium sulfite, lithium sulfate potassium chloride, calcium bicarbonate, sodium sulfate, calcium sulfate, potassium acid phosphate, calcium lactate, d-mannitol, urea, inositol, magnesium succinate, tartaric acid, carbohydrates such as raffinose, sucrose, glucose, α-d-lactose monohydrate, and mixtures thereof. The compound is initially present in excess and it can be in any physical form such as particle, crystal, pellet, tablet, strip, film or granule. The osmotic pressure of saturated solutions of various osmotically effective compounds and for mixtures of compounds at 37° C., in water, is listed in Table 2. In the table, the osmotic pressure $\pi$, is in atmospheres, ATM. The osmotic pressure is measured in a commercially available osmometer that measures the vapor pressure difference between pure water and the solution to be analyzed, and according to standard thermodynamic principles, the vapor pressure ratio is converted into osmotic pressure difference. In Table 2, osmotic pressures of from 20 ATM to 500 ATM are set forth; of course, the invention includes the use of lower osmotic pressures from zero, and higher osmotic pressures than those set forth by way of example in Table 2. The osmometer used for the present measurements is identified as Model 302B, Vapor Pressure Osmometer, manufactured by the Hewlett Packard Co., Avondale, Penna.

TABLE 2

| COMPOUND OR MIXTURE | OSMOTIC PRESSURE ATM |
| --- | --- |
| Lactose-Fructose | 500 |
| Dextrose-Fructose | 450 |
| Sucrose-Fructose | 430 |
| Mannitol-Fructose | 415 |
| Sodium Chloride | 356 |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Mannitol-Sucrose | 170 |
| Dextrose | 82 |
| Potassium Sulfate | 39 |
| Mannitol | 38 |
| Sodium Phosphate Tribasic . 12H$_2$O | 36 |
| Sodium Phosphate Dibasic . 7H$_2$O | 31 |
| Sodium Phosphate Dibasic . 12H$_2$O | 31 |
| Sodium Phosphate Dibasic Anhydrous | 29 |
| Sodium Phosphate Monobasic . H$_2$O | 28 |

The expression "active agent" as used herein broadly includes any compound, composition of matter or mixture thereof, that can be delivered from the system to produce a beneficial and useful result. The agent can be soluble in fluid that enters the reservoir and functions as an osmotically effective solute or it can have limited solubility in the fluid and be mixed with an osmotically effective compound soluble in fluid that is delivered from the system. The active agent includes pesticides, herbicides, germicides, biocides, algicides, rodenticides, fungicides, insecticides, anti-oxidants, plant growth promoters, plant growth inhibitors, preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, microorganism attenuators, and other agents that benefit the environment of use.

In the specification and the accompanying claims, the term "drug" includes any physiologically or pharmacologically active substances that produce a localized or systemic effect or effects in animals, including mammals, humans and primates, avians, domestic household, sport or farm animals such as sheep, goats, cattle, horses and pigs, for administering to laboratory animals such as mice, rats and guinea pigs, and to fishes, reptiles and zoo animals. The term "physiologically" as used herein denotes the administration of drug to produce normal levels and functions. The term "pharmacologically" denotes variations in response to amounts of drug including therapeutic. Stedman's Medical Dictionary, 1966, published by Williams & Wilkins, Baltimore, Md. The active drug that can be delivered includes inorganic and organic compounds without limitation, those materials that act on the central nervous system such as hypnotics and sedatives, including pentobarbital sodium, phenobarbital, secobarbital, thiopental and mixtures thereof, heterocyclic hypnotics such as dioxopiperidines and glutarimides, hypnotics and sedatives such as amides and ureas, exemplified by diethylisovaleramide and α-bromoisovaleryl urea, hypnotic and sedative urethanes and disulfantes, psychic energizers such as isocoboxazid, nialamide, phenelzine, imipramine, tranylcypromine and pargylene, tranquilizers such as chloropromazine, promazine, fluphenazine, reserpine, deserpidine, meprobamate, benzodiazepines such as chlordiazepoxide, anticonvulsants such as primidone, enitabas, diphenylhydantoin, ethltion, pheneturide and ethosuximide, muscle relaxants and antiparkinson agents such as mephenesin, methocarbomal, trihexylphenidyl, biperiden, levo-dopa also known as L-dopa and L-β-3-4-dihydroxypehnylalanine, analgesics such as morphine, codeine, meperidine, nalorphine, antipyretics and anti-inflammatory agents such as aspirin, salicylamide, colchicine and sodium salicylamide, local anesthetics such as procaine, lidocaine, maepaine, piperocaine, tetracaine and dibucane, antispasmodics and muscle contractants such as atropine, scopolamine, methscopolamine, oxyphenonium, papaverine, prostaglandins such as $PGE_1$, $PGE_2$, $PGF_{1\alpha}$, $PGF_{2\alpha}$ and PGA, anti-microbials such as penicillin, tetracycline, oxytetracycline, chlorotetracycline, chloramphenicol and sulfonamides, anti-malarials such as 4-aminoquinolines, 8-aminoquinolines and pyrimethamine, hormonal agents such as prednisolone, cortisone, cortisol and triamcinolone, androgenic steroids such as methyltestosterone, and fluoxmesterone, estrogenic steroids such as 17β-estradiol, α-estradiol, estriol, α-estradiol 3-benzoate, and 17-ethynyl estradiol-3-methyl ether, progestational steroids such as progesterone, 19-nor-pregn-4-ene-3,20-dione, 17-hydroxy-19-nor-17-α-pregn-5(10)-ene-20-yn-3-one, 17α-ethynyl-17-hydroxy-5(10)-estren-3-one, and 9β,10α-pregna-4,6-diene-3,20-dione, sympathomimetic drugs such as epinephrine, amphetamine, ephedrine and norepinephrine, cardiovascular drugs such as procainamide, procainamide hydrochloride, amyl nitrile, nitroglycerin, dipyredamole, sodium nitrate and mannitol nitrate, diuretics such as chlorathiazide, acetazolamide, methazolamide and flumethiazide, antisparasitics such as bephenium, hydroxynaphthoate, dichlorophen and dapsone, neoplastics such as mechlorethamine, uracil mustard, 5-fluorouracil, 6-thioguanine and procarbazine, hypoglycemic drugs such as insulin, isophane insulin, protamine zinc insulin suspension, globin zinc insulin, extended insulin zinc suspension, tolbutamide, acetohexamide, tolazamide and chlorpropamide, nutritional agents such as ascorbic acid, niacin, nicotinamide, folic acid, choline, biotin, pantothenic acid, and vitamin $B_{12}$, essential amino acids, essential fats, eye drugs such as pilocarpine, polocarpine salts such as pilocarpine nitrate, pilocarpine hydrochloride, dichlorphenamide, atropine, atropine sulfate, scopolamine and eserine salicylate, and electrolytes such as calcium gluconate, calcium lactate, potassium chloride, potassium sulfate, sodium chloride, potassium fluoride, sodium fluoride, ferrous lactate, ferrous gluconate, ferrous sulfate, ferrous fumurate and sodium lactate. The beneficial drugs are known to the art in *Remington's Pharmaceutical Sciences*, 14th Ed., 1970, published by Mack Publishing Co., Easton, Penna.; and in *The Pharmacological Basis of Therapeutics*, by Goodman and Gilman, 4th Ed., 1970, published by The MacMillian Company, London.

The drug can also be in various forms, such as uncharged molecules, molecular complexes, pharmacologically acceptable salts such as hydrochlorides, hydrobromides, sulfate, laurylate, palmitate, phosphate, nitrate, borate, acetate, maleate, tartrate, oleate, and salicylate. For acidic drugs, salts of metals, amines or organic cations, for example quaternary ammonium can be used. Derivatives of drugs such as esters, ethers and amides which have solubility characteristics suitable for use herein can be used alone or mixed with other drugs. Also, a drug that is water insoluble can be used in a form that is a water soluble derivative thereof to effectively serve as a solute, and on its release from the device, is converted by enzymes, hydrolyzed by body pH or other metabolic processes to the original form, or to a biologically active form. The agent can be in the reservoir as a solution, dispersion, paste, cream, particle, granule, emulsion, suspension or powder. Also, the agent can be mixed with a binder, dispersant, emulsifier or wetting agent and dyes.

The amount of agent present in the system is initially in excess of the amount that can be dissolved in the fluid that enters the reservoir. Under this physical state when the agent is in excess, the system will osmotically operate to give a substantially constant rate of release. The rate of agent release pattern can also be varied by having different amounts of agent in the reservoir to form solutions containing different concentrations of agent for delivery from the device. Generally, the system can house from 0.05 ng to 5 grams or more, with individual systems containing for example, 25 ng, 1 mg, 5 mg, 250 mg, 500 mg, 1.5 g, and the like.

The solubility of an agent in an external fluid can be determined by various art known techniques. One method consists of preparing a saturated solution comprising the external fluid plus the agent as ascertained by analyzing the amount of agent present in a definite quantity of the fluid. A simple apparatus for this purpose consists of a test tube of medium size fastened upright in a water bath maintained at constant temperature and pressure, for example, one atmosphere, in which the fluid and agent are placed and stirred by a motor driven rotating glass spiral. After a given period of stirring, a definite weight of the fluid is analyzed and the stirring continued for an additional period of time. If the analysis shows no increase of dissolved agent after successive periods of stirring, in the presence of excess solid agent in the fluid, the solution is saturated and the results are taken as the solubility of the product in the fluid. If the agent is soluble, an added osmotically effective compound optionally may not be needed; if the agent has limited solubility in the fluid, then an osmotically effective compound can be incorporated into the device. Numerous other methods are available for the determination of the solubility of an agent in a fluid. Typical methods used for the measurement of solubility are chemical analysis, ultra violet spectometry, density, refractive index and electrical conductivity. Details of various methods for determining solubilities are described in *United States Public Health Service Bulletin*, No. 67 of the Hygenic Laboratory; *Encyclopedia of Science and Technology*, Vol. 12, pages 542 to 556, 1971, published by McGraw-Hill, Inc.; and *Encyclopaedic Dictionary of Physics*, Vol. 6, pages 547 to 557, 1962, published by Pergamon Press, Inc.

The systems of the invention are manufactured by standard techniques. For example, in one embodiment, the agent and other ingredients that may be housed in the compartment and a solvent are mixed into a solid, semisolid or gel form by conventional methods such as ballmilling, calendering, stirring, or rollmilling and then pressed into a preselected shape. The laminae forming the system can be applied by molding, spraying or dipping the pressed shape into wall forming materials. In another embodiment, the laminae can be cast into films, shaped to the desired dimensions, an exterior lamina sealed to an interior lamina to define a compartment that is filled with agent and then closed. The system also can be manufactured with an empty compartment that is filled through the passageway. The system when formed of more than one laminate, joined by various joining techniques such as high frequency electronic sealing that provides clean edges and firmly sealed systems. Another, and presently preferred, technique that can be used to apply laminae to a compartment is the air suspension procedure. This procedure consists in suspending and tumbling the pressed agent in a current of air and a lamina composition until the lamina is applied to the agent. The procedure is repeated with a different lamina to form the laminate. The air suspension procedure is described in U.S. Pat. No. 2,799,241; *J. Am. Pharm. Assoc.*, Vol. 48, pages 451 to 459, 1979; and ibid, Vol. 49, pages 82 to 84, 1960. Other standard manufacturing procedures are described in *Modern Plastics Encyclopedia*, Vol. 46, pages 62 to 70, 1969; and in *Pharmaceutical Sciences*, By Remington, Fourteenth Edition, Pages 1626 to 1678, 1970, published by Mack Publishing Company, Easton, Penna.

Exemplary solvents suitable for manufacturing the laminates and laminae include inert inorganic and organic solvents that do not adversely harm the materials and the final laminated wall. The solvents broadly include members selected from the group consisting of aqueous solvents, alcohols, ketones, esters, ethers, aliphatic hydrocarbons, halogenated solvents, cycloaliphatic, aromatics, heterocyclic solvents and mixtures thereof. Typical solvents include acetone, diacetone alcohol, methanol, ethanol, isopropyl alcohol, butyl alcohol, methyl acetate ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol.

The following examples are merely illustrative of the present invention, and they should not be considered as limiting the scope of the invention in any way, as these examples and other equivalents thereof will become apparent to those versed in the art in the light of the present disclosure, the drawings and the accompanying claims.

EXAMPLE 1

Figure 11:
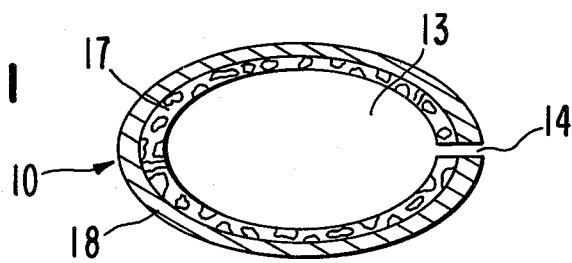
FIG. 11 is a cross-section through the osmotic system of FIG. 1, designed as an oval oral system.

The delivery rate from an osmotic system 10 made according to the invention, which system 10 is illustrated in opened section in FIG. 11 is given by equation (1), wherein dm is the mass per unit time dt.

$$\left(\frac{dm}{dt}\right)_t = \frac{A \cdot S}{R_t} \qquad (1)$$

In equation (1), A is the system laminated area, S is the solubility of the agent and $R_t$ is the resistance of the laminated wall to the passage of water, which is further defined by equation (2).

$$R_t = R_1 + R_2 \qquad (2)$$

In equation (2), $R_1$ is the resistance of microporous lamina 17 and $R_2$ is the resistance of semipermeable lamina 18. The resistances of $R_1$ and $R_2$ are given by equations (3) and (4) as follows:

$$R_1 = \frac{h_1}{D_1 \epsilon/\tau} \qquad (3)$$

$$R_2 = \frac{h_2}{(k\pi)_2} \qquad (4)$$

In equations (3) and (4) $h_1$ and $h_2$ are respectively the thickness of microporous lamina 17 and semipermeable lamina 18, $D_1$ is the diffusion coefficient of water, $\epsilon$ is the porosity of microporous lamina 17 and $\tau$ is the tortuosity of microporous lamina 17. In equation (4) $(K\pi)_2$ is the water transmission rate through semipermeable lamina 18 in equation (2) and further defined by equation (5) as follows:

$$\frac{dv}{dt} = (k\pi)_2 \frac{A}{h_2} \qquad (5)$$

wherein dv/dt is the volume flux through semipermeable lamina 18 of thickness $h_2$ with a surface area A.

The total delivery rate (dm/dt) from system 10 can be scientifically determined from equations (1) through (4) as given by equation (6) as follows:

$$\left(\frac{dm}{dt}\right)_t = \frac{A \cdot S}{\frac{h_1}{D_1 \epsilon/\tau} + \frac{h_2}{(k\pi)_2}} \qquad (6)$$

The drug solubility S, and dimensions A, h, and $h_2$ are easily determined by procedures described above and by conventional laboratory measurements. The quantity $(k\pi)_2$ is obtained from osmosis measurement so that only the expression $D_1 \epsilon/\tau$ need to be defined. Since the microporous lamina can be laminated onto drug reservoirs, two methods are presented which can be used to fully characterize the resistance of $R_1$.

Method 1: Determination of $R_1$ from drug diffusion experiments.

From the Stokes-Einstein relationship, *Concise Dictionary of Physics*, Thewlis, J., page 314, 1973, published by Pergamon Press, New York, it is known the diffusion coefficient D of molecules with radius r and molecular weight M are related by equation (7) as follows:

$$D \sim \frac{1}{r} \sim \frac{1}{M^{\frac{1}{3}}} \tag{7}$$

It follows therefore that the ratio of the diffusion coefficient of water $D_1$ to the diffusion coefficient of drug $D_D$ is given by equation (8) as follows:

$$D_1 = D_D \left(\frac{M_D}{M_1}\right)^{\frac{1}{3}} \tag{8}$$

wherein $M_1$ is the molecular weight of water and $M_D$ is the molecular weight of the drug. By multiplying both sides of equation (8) by $\epsilon/\tau$ the relationship between the resistance of the microporous lamina to water $R_1$ and to drug $R_D$ is given by equation (9).

$$R_1 = R_D \left(\frac{M_1}{M_D}\right)^{\frac{1}{3}} \tag{9}$$

The resistance $R_D$ is calculated by measuring the zero order release rate of drug, $(dm/dt)_D$ by diffusion, from drug reservoirs laminated with a microporous lamina, expressed by equation (10) as follows:

$$\left(\frac{dm}{dt}\right)_D = D_D \cdot \frac{\epsilon}{\tau} \cdot \frac{A}{h_1} \cdot s \tag{10}$$

Here $R_D$ is defined by equation (11) as follows:

$$R_D = \frac{h_1}{D_D \epsilon/\tau} \tag{11}$$

An additional refinement of the method can be advantageously used by expressing the diffusion coefficient as a function of the molecular weight by equation (12) as seen in *Biochemica et Biophysica Acta*, Vol 5, page 358, 1950, as follows:

$$D = f(M) \tag{12}$$

$$f(M) = \frac{a}{M^{\frac{1}{3}}} + \frac{b}{M^{\frac{1}{2}}} + \frac{C}{M} + \left(\frac{Cm^2}{sec}\right) \tag{13}$$

wherein $a = 2.74 \times 10^{-5}$, $b = 1.65 \times 10^{-5}$, $c = 17 \times 10^{-5}$. Using equation (12) rather than equation (8) results in equation (14):

$$R_1 = R_D \times \frac{f(M_1)}{f(M_D)} \tag{14}$$

wherein $R_D$ is calculated from equation (10), $f(M_1)$ and $f(M_D)$ are calculated from equations (13) and (14) by substituting the appropriate molecular weights $M_1$ and $M_D$.

Method 2. Determination of $R_1$ from the comparison of release rates from a series of microporous-semipermeable laminated walls and semipermeable laminated systems.

Figure 12:
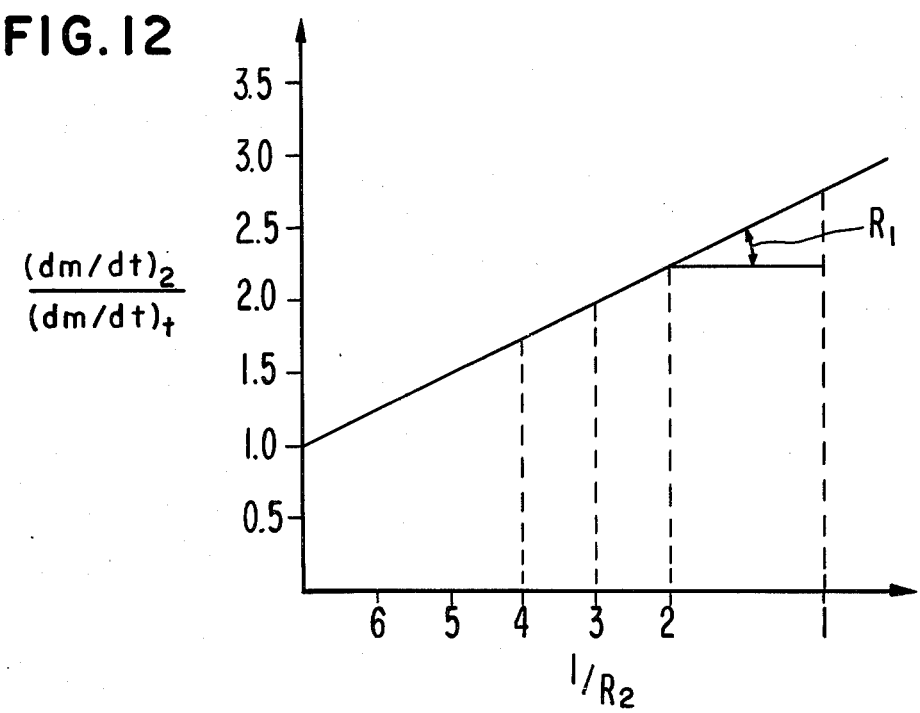
FIG. 12 and FIG. 13 represent the drug delivery rate ratio for osmotic systems made without to systems made with microporous lamina having equal semipermeable lamina thickness, as a function of semipermeable lamina resistance.

The release rate of an osmotic system manufactured only with a semipermeable wall (2) is given by equation (15) as follows:

$$\left(\frac{dm}{dt}\right)_2 = \frac{A \cdot S}{R_2} \tag{15}$$

with $$R_2 = \frac{h_2}{(K\pi)_2} \tag{16}$$

which, when compared to a system 10 with the same drug reservoir but manufactured with an additional microporous lamina 17 the ratio of rates from equations (1), (2) and (15) is given by equation (17) as follows:

$$\frac{(dm/dt)_2}{(dm/dt)_t} = 1 + \frac{R_1}{R_2} \tag{17}$$

wherein $R_1$ can be calculated from the graph illustrating $(dm/dt)_2/(dm/dt)_t$ vs $1/R_2$ as seen in FIG. 12 wherein the expression $(dm/dt)_2$ is the semipermeable lamina, $(dm/dt)_t$ is the laminated wall comprising a semipermeable and microporous lamina, the numbers on the x axis are values of $1/R_2$ indicated by sample numbers and the numbers on the y axis are the ratio of the two release rates defined by the expressions, and $R_1$ is then the slope of the straight line.

FIG. 12 is obtained as follows: therapeutic osmotic systems 10, comprising a drug reservoir surrounded with a microporous lamina, and systems 10 comprising of only a drug reservoir ar laminated with a semipermeable lamina prepared in an air suspension machine, from which they are taken at successive time intervals, 1, 2, 3, etc. as seen in FIG. 12. Systems of any time interval 1, 2, 3, etc. have equal values of $R_2$. The values for $R_2$ of the successive samples, 1, 2, 3, etc. are calculated from equation (15) on measuring $(dm/dt)_2$. Successive values $(dm/dt)_t$ are also measured for the laminated system having the microporous and semipermeable laminated wall, such that the ratio $(dm/dt)_2/(dm/dt)_t$ can be calculated for each value of $R_2$ and plotted as shown in FIG. 12. The resistance of the microporous lamina $R_1$ is then obtained from the slope of the straight line which intersects the ordinate at value of 1.

EXAMPLE 2

An osmotic therapeutic system for the controlled and continuous release of the beneficial agent potassium chloride was made as follows: first, 500 mgs of commercially available potassium chloride was compressed by standard compression techniques using a ⅜ inch concave punch, to yield a compressed mass of 2.3 cm². Next, a plurality of pressed masses weight 2 kgs were placed in a Wurster air suspension coating machine with a semipermeable lamina forming material. The lamina forming solution containing the semipermeable material was prepared by dissoving 116 g of cellulose acetate having a 32% acetyl content in 2204 g of acetone:water in the ratio of 88.5:11.5 by weight, with the solution prepared by using a high speed Waring blender. The semiperemable lamina had a thickness of 4 mils.

Next, a microporous forming lamina was laminated to the surface of the semipermeable lamina. The microporous lamina was applied from a solution prepared by mixing 48 g of cellulose acetate having an acetyl content of 32% with 32 g of sorbitol in 1520 g of acetone:water solvent having a 80:20 ratio by weight. The ingredients were mixed in a high speed blender. The microporous lamina was applied to the system until it had a thicknes of 3 mils. The osmotic systems were dried in an oven at 50° C. until the solvent was evaporated from the laminated wall.

Finally, a portal having a diameter of 10.5 mils was mechanically drilled through the 7 mil thick laminated wall to yield the osmotic system. The laminated wall maintains its physical and chemical integrity in the presence of the drug and the system has a continuous rate of release of 34 mgs per hour over a prolonged period of 14 hours.

EXAMPLE 3

A plurality of osmotic therapeutic systems are manufactured according to the procedure of Example 2, wherein the conditions are as described except that the drug of Example 2 is replaced with an orally administrable drug selected from the group consisting of methazolamide, ethoxyolamide, diazepan, amitriptylene hydrochloride, imipramine hydrochloride, nacin, benzthiazide, chlorothiazide, tolbutamide, tolazamide, chloropropamide, procainamide hydrochloride, colchicine, and atropine, along with an osmotically effective solute selected from the group consisting of sodium chloride, mannitol and glucose.

EXAMPLE 4

A plurality of osmotic therapeutic systems are manufactured according to the procedures of Examples 1 and 2 with all conditions as described except that the semipermeable lamina was formed by using a semipermeable material selected from the group consisting of cellulose acetate propionate, cellulose acetate butyrate, cellulose acetate benzoate, and cellulose acetate propylcarbamate.

EXAMPLE 5

An osmotic therapeutic system designed for orally releasing lithium sulfate is prepared according to the following parameters: (a) the water transmission rate of cellulose acetate having an acetyl content of 32% and using lithium sulfate as the osmotic driving agent is $$0.05 \frac{cm^3 \cdot mil}{cm^2 \cdot hr};$$

(b) the plasticized film of cellulose acetate having an acetyl content of 32% and a polyethylene glycol 400 content of 10% has a water transmission value with lithium sulfate as the osmotic attractant of $$0.1 \frac{cm^3 \cdot mil}{cm^2 \cdot hr};$$

(c) therefore, a 60 mg per hour release rate of lithium sulfate the wall of the system would have a thickness of $$h = \frac{A \times S \times K\pi}{dm/dt}, \text{ or } h = \frac{1.92 \times 310 \times 1}{60},$$

for a thickness of 1 mil.

Osmotic therapeutic systems having a single semipermeable wall of 1 mil thick could not endure the mechanical insult present in the environment of use and they need a supportive means. A strong, substantially rigid microporous lamina with zero resistance to water transport supports a thin semipermeable lamina and unexpectedly produce the desired delivery rate.

Next, drug reservoirs were prepared by screening a composition of 95% lithium sulfate and 5% poly(vinylpyrrolidone) in ethanol:water, 90:10 by volume, through a 30 mesh screen and then dried to remove the solvent. Then, the dried composition was passed through a 40 mesh screen and the screened product mixed with 1% magnesium stearate. Reservoirs of 400 mgs each were compressed with a 5/16 inch concave punch in a Manesty press tableting machine using the final screened composition containing the magnesium stearate. The reservoirs had an area of 1.92 cm². The desired release rate dm/dt of 60 mg/hr for systems having a semipermeable lamina of 1 mil and a microporous lamina of 5 mils is obtained by preparing the system as follows: first, 2 kg of lithium sulfate reservoirs were placed in an air suspension machine and surrounded with a microporous lamina until a 5 mil thick lamina was applied to each reservoir. The microporous lamina forming solution was prepared by mixing 88.8 g of cellulose acetate having an acetyl content of 38.3% with 22.2 g of polyethylene glycol and 111 g of sorbitol in acetone:water, 78:22% by weight, until a clear solution was obtained. The solvent had a final volume of 4310 ml and it consisted of 3450 ml of acetone and 770 ml of water.

To the microporous lamina was then applied a semipermeable lamina, which lamina had a thickness of 1 mil. The semipermeable lamina forming solution was prepared by blending 27 g of cellulose acetate having an acetyl content of 32% and 3 g of polyethylene glycol 400 in a high speed blender using acetone:water, 90:10, as the solvent. These polymeric solutions contained 2% solids.

The laminated osmotic systems were dried in an oven to remove the solvent, and then a 7.9 mil portal was drilled through the wall. The final systems had a controlled and continuous rate of release of 58 mgs per hr over a prolonged period of 7 hrs.

EXAMPLE 6

A plurality of osmotic therapeutic systems were manufactured according to the procedure of Example 5 with all conditions as described except that the lamina forming the semipermeable lamina is replaced with a semipermeable lamina selected from the group consisting of cellulose propionate having a propionyl content of 38.5%, cellulose acetate propionate having an acetyl content of 1.5 to 7% and a pripionyl content of 39 to 42%, and cellulose acetate butyrate having an acetyl content of 13 to 15% and a butyryl content of 34 to 39%. The laminates are effected by using the air suspension techniques described in *J. Pharm. Sci.*, Vol. 53, No. 8, pages 877 to 881, 1964 and ibid, Vol. 53, No. 8, pages 953 to 955, 1964.

EXAMPLE 7

A series of osmotic systems were made according to the procedure of Example 1, Method 2, to ascertain the resistance to water transport for microporous laminae. The osmotic systems were constructed for the controlled delivery of the drug acetazolamide. The systems contained drug cores of sodium acetazolamide with an equivalency of 500 mg of acetazolamide. This example also demonstrates the inventive use of microporous lamina as supporting means for semipermeable lamina used for the manufacture of operative, osmotic therapeutic systems.

The osmotic systems were made as follows: first, capsular-shaped drug cores of acetazolamide were made with and without a microporous lamina, $MP_1$. Next, the uncoated cores and the microporous lamina coated cores were coated with a semipermeable lamina $h_2$. The resistance $R_2$ for semipermeable lamina and the semipermeable microporous laminate, $R_2$, were calculated from the weight of the sempermeable lamina. The values for $h_2$ and $R_2$ are listed in Table 3.

Figure 13:
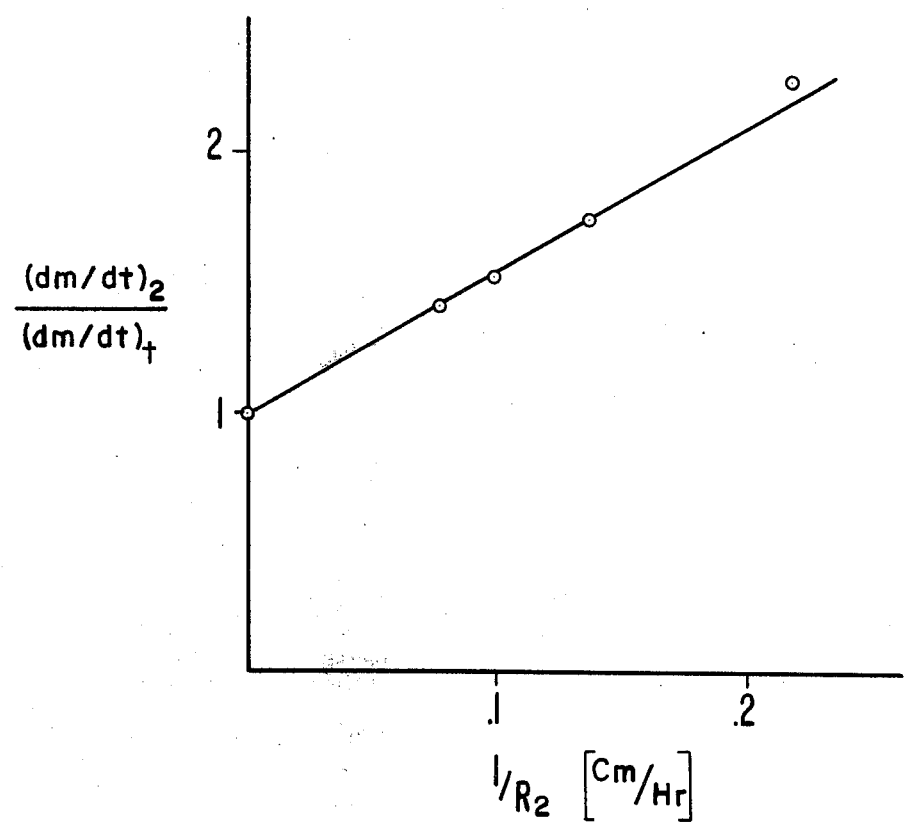

In Table 3, $(dm/dt)_2$ is the release rate for sodium acetazolamide coated with a semipermeable lamina and measured in physiological saline; $(dm/dt)_t$ is the release rate for sodium acetazolamide coated with a laminate consisting of a microporous lamina and a semipermeable lamina measured in physiological saline; $h_1$ is the thickness of the microporous lamina, 5.14 mils; $h_2$ is the thickness of the semipermeable lamina laminated on the microporous lamina; $R_1$ is the resistance to water transport of the microporous lamina having a thickness $h_1$ of 5.14 mils where $R_1$ equals 5.55 hr/cm as calculated from the slope of FIG. 13. The microporous lamina of the system consisted of 55% cellulose acetate having an acetyl content of 38.3% and 45% sorbitol. The microporous lamina was coated from a solvent consisting of acetone:water, 79:21% by weight. The semipermeable lamina consisted of 58.7% cellulose acetate having an acetyl content of 32%, 26% cellulose acetate having an acetyl content of 38.3% and 15% sorbitol. The lamina was coated from the above solvent.

TABLE 3

Release Rates and Laminae Resistances To Water Transport For Drug Delivery Systems.

| $(dm/dt)_2$ mgs/hr | $1/R_2$ (cm/hr) | $(dm/dt)_t$ mgs/hr | $h_2$ mils | $(dm/dt)_2 / (dm/dt)_t$ |
|---|---|---|---|---|
| 100 | $7.74 \times 10^{-2}$ | 70 | 2.3 | 1.42 |
| 123 | $9.9 \times 10^{-2}$ | 80 | 1.83 | 1.53 |
| 174.7 | $13.5 \times 10^{-2}$ | 100 | 1.1 | 1.76 |
| 279 | $21.6 \times 10^{-2}$ | 120 | 0.65 | 2.32 |

EXAMPLE 8

The procedures of Examples 5 and 6 are repeated in this example and all conditions are as described except that the system is sized, shaped and adapted as an ocular therapeutic system, the microporous laminae forms in situ continuous pathes pores in the lamina, and the drug in the reservoir is replaced by a member selected from the group consisting of idoxuridine, phenylephrine, pilocarpine hydrochloride, eserine, carbachol, phospholine iodine, and demecarine bromide, each mixed with an osmotically effective solute selected from the group consisting of sodium bicarbonate, sodium chloride and a glucose-mannitol mixture.

EXAMPLE 9

A vaginal drug delivery osmotic system shaped like a tampon and suitable for releasing a vaginally administrable locally or systemically acting drug which drug exhibits an osmotic pressure gradient across a laminated wall, is made by first surrounding a vaginal drug reservoir with a 10 mil thick microporous producing lamina characterized by forming in situ a lamina having a porosity of 60% and a pore size of 0.45 microns, and then laminating to the microporous lamina with a 2 mil thick semipermeable producing lamina that exhibits chemical and physical inertness in the vagina. The system has a 7 to 8 mil diameter portal for release of drug.

EXAMPLE 10

An oral, osmotic therapeutic system for releasing theophylline monoethanolamine over a six to seven hour therapeutic period is manufactured as follows: first, a multiplicity of compressed drug cores are formed in a conventional Manesty tableting machine for lamination. The machine uses a 5/16 inch diameter concave punch to produce cores having a hardness of about 8.4 kg as measured by a Strong-Cobb hardness tester. The cores have an area of 1.45 $cm^2$ and each core contained about 125 mg of theophylline. The cores were placed in a Wurster air suspension machine that air tumbled the cores until they are uniformly coated with a laminated wall. The laminated wall has an inner lamina facing the drug reservoir and an outer lamina distant from the reservoir or drug compartment.

The laminae are consecutively coated with the Wurster machine to form an integral, laminated wall. The inner lamina is coated from a composition comprising 116 g of cellulose acetate having an acetyl content of 38.3% homogenously mixed with 95 g of sorbitol. The two materials were thoroughly blended and then a solvent was added consisting of 80 parts of acetone and 10 parts of water, 4298 ml of acetone and 845 ml of water were used. The inner lamina had a final thickness of 4.5 mils.

The outer lamina was permanently laminated onto the inner lamina from a semipermeable blend prepared as follows: to 34.8 g of cellulose acetate having an acetyl content of 38.3% was added 34.8 g of cellulose acetate having an acetyl content of 32% and 104 g of sorbitol and the three ingredients blended with 1520 g of acetone:water (90:10 by wt) solvent in a Waring blender until a uniform lamina forming composition was produced. The semipermeable lamina was intimately and firmly laminated to the outer surface of the microporous lamina using the air suspension technique described above.

Finally, a 10 mil exit portal was drilled through the laminated wall. The laminated osmotic system keeps its physical and chemical integrity in the test environment and in the presence of drug, and it had a continuous rate of release of 15 mgs per hour over a prolonged period of 7 hours.

EXAMPLE 11

The procedure of Example 10 is repeated, but the drug in the compartment is replaced with a member selected from the group consisting of nicotinamide, mannitol hexanitrate, isocarboxyazid, triamicolone, salicylamide, aspirin and aminophylline, each mixed with an osmotically effective solute having an osmotic pressure of from 170 to 500 atm.

EXAMPLE 12

An osmotic, therapeutic system for the controlled and continuous oral release of the beneficial agent theophylline monoethanolamine is made as follows: first, 1.8 kgs of theophylline monoethanolamine drug cores, each having an area of 2.3 cm$^2$ and a mass of 250 mg of theophylline, were prepared by compressing the drug in a conventional Manesty machine using a ⅜ inch diameter concave punch. The cores have a hardness of about 9 kg, as measured by a Strong-Cobb hardness tester.

The laminated wall that surrounds each drug core comprising the reservoir was manufactured as follows: first, an inner microporous lamina producing blend was made by blending 90 g of cellulose acetate having an acetyl content of 39.8% with 90 grams of sorbitol in 2820 g of acetone:water solvent, 78:22% by weight, until a workable blend was produced. The blend was applied to drug reservoirs using the air suspension machine described above, to yield the microporous lamina having a zero resistance to the passage of water and biological fluid.

Next, an outer semipermeable lamina that is a rate controlling lamina and is permeable to the passage of fluid and impermeable to the passage of drug and compounds present in the environment of use was prepared by homogenously blending 45 g of cellulose acetate having an acetyl content of 38.3%, with 45 g of cellulose acetate having an acetyl content of 32% and 10 g of d-glucitol in 2400 g of acetone:water solvent, 90:10 by weight, in a high shear blender until a homogenous blend was produced. The blend was laminated onto the exterior surface of the microporous lamina to form a semipermeable lamina 2.4 mils thick. A 10.5 mil portal was drilled through the laminated wall for releasing drug from the system. The system released 20 mgs per hr of drug over a 12 hr period.

EXAMPLE 13

The procedure of Example 10 is repeated with all lamination procedures as described, but the drug in the compartment is replaced with a member selected from the group consisting of calcium gluconate, calcium lactate, potassium sulfate, potassium fluoride, sodium fluoride, ferrous lactate, ferrous gluconate, ferrous sulfate, ferrous fumurate and sodium lactate, which drugs are released in an effective amount at a controlled and continuous rate over a prolonged period of time.

EXAMPLE 14

An osmotic, therapeutic system for the controlled and continuous oral release of the beneficial agent sodium acetazolamide is made as follows: first, 2 kgs of sodium acetazolamide was compressed in a conventional Manesty machine using a 7/16 inch diameter concave punch to yield a drug core having an area of 3.36 cm$^2$. Then, the core was coated in an air suspension machine with a 7.5 mil thick microporous lamina formed from a composition comprising 115 g of cellulose acetate having an acetyl content of 38.3% and 45.1 g of sorbitol. The coat was applied by the air suspension technique and the microporous lamina described above.

Next, a semipermeable lamina was firmly coated onto the microporous lamina. The semipermeable lamina was applied from a semipermeable lamina forming composition comprising 42.08 g of cellulose acetate having an acetyl content of 32%, 49.35 g of cellulose acetate having an acetyl content of 38.3% and 16.16 g of di-glucitol. The lamina was formed from a solvent consisting of 2045 g of acetone:water, 90:10 by weight. The semipermeable lamina had a thickness of 0.5 mils. The system released 40 mgs per hour of drug through a 10 mil passageway over a period of 15 hours.

EXAMPLE 15

An osmotic, therapeutic system for the controlled and continuous oral release of sodium acetazolamide is made as follows: first 170 grams of sodium acetazolamide and 8.5 grams of 5% polyvinylpyrrolidone in isopropyl alcohol are blended in a standard v-blender for 45 minutes to produce wet granules. The granules are dried in an oven at 50° C. for 48 hours and passed through a standard No. 30 mesh sieve. Then, 1.8 grams of magnesium stearate is separately passed through the No. 30 sieve and the granules are mixed with the magnesium stearate in the blender for about 30 minutes, or until a uniform mixture is obtained. The mixture is then compressed in a conventional Manesty machine using a 5/16 inch diameter concave punch to produce drug cores. The cores have a hardness of about 9 kgs, as measured by a Strong-Cobb hardness tester. The cores contain 125 mgs of acetazolamide and have an area of 1.4 cm$^2$.

The laminated wall is prepared as follows: first, a semipermeable lamina forming blend is prepared by blending 90% cellulose acetate having an acetyl content of 38.3% and 10% polyethylene glycol having a molecular weight of 400 in sufficient acetone to produce a 5% polymeric solution. Next, an outer microporous forming lamina is prepared by blending 115 g of cellulose acetate having an acetyl content of 38.3% and 95.1 g of sorbitol in 3972 g of acetone:water solvent.

Then, the drug cores prepared above are placed in a Wurster air suspension machine. The cores are air tumbled first with the semipermeable lamina until they are uniformly coated with the inner lamina forming solution. The coated cores were dried in an oven at 50° C. for one week to evaporate the solvent. Next, the dried cores are returned to the Wurster machine and coated with the outer microporous lamina forming solution. The laminated product was dried as described. Finally, a 7.5 mil passageway was mechanically drilled through the laminated wall.

The novel osmotic systems of this invention use means for the obtainment of precise release rates in the environment of use while simultaneously maintaining the integrity of the device. While there has been described and pointed out features of the invention as applied to presently preferred embodiments, those skilled in the art will appreciate that various modifications, changes, additions, and omissions in the systems illustrated and described can be made without departing from the spirit of the invention.

I claim:

1. An osmotic therapeutic system for the controlled dispensing of a beneficial drug formulation to a biological fluid environment of use comprising:
    (a) a shaped laminated wall comprising: a semipermeable lamina that is formed of a material permeable to the passage of an external fluid, substantially impermeable to the passage of drug, and essentially maintains its physical and chemical integrity in the biological environment of use, said semipermeable lamina in laminar arrangement with a lamina formed of a material that forms in the environment of use a microporous lamina having a plurality of micropores with paths through the lamina, said laminated wall surrounding and forming:

(b) a compartment containing a beneficial drug formulation;

(c) a passageway in the laminated wall communicating with the compartment and the exterior of the system for dispensing drug formulation from the system; and, (d) wherein in operation, when the system is in the environment of use, fluid from the environment is imbibed through the laminated wall into the compartment in a tendency towards osmotic equilibrium at a rate determined by the permeability of the laminated wall and the osmotic pressure gradient across the laminated wall, thereby forming a solution containing the drug formulation that is dispensed through the passageway at a controlled rate over a prolonged period of time.

2. The osmotic therapeutic system for dispensing drug according to claim 1, wherein the drug is a member selected from the group of drugs that are soluble in the fluid and exhibit an osmotic pressure gradient across the laminated wall, and from the drugs that have limited solubility in the fluid which drug is mixed with an osmotically effective solute that is soluble in the fluid and exhibits an osmotic pressure gradient across the laminated wall against the fluid.

3. The osmotic therapeutic system for dispensing drug according to claim 1, wherein the semipermeable lamina additionally comprises a member selected from the group consisting of a stabilizing material that imparts integrity to the lamina, a flux regulator that aids in controlling the permeability of the lamina, a plasticizer that imparts flexibility to the lamina, a dispersant that aids in forming the lamina, and mixtures thereof.

4. The osmotic therapeutic system for dispensing drug according to claim 1, wherein the material forming the semipermeable lamina is a member selected from the group consisting of cellulose acylates, cellulose diacylates, and cellulose triacylates.

5. The osmotic therapeutic system for dispensing drug according to claim 1, wherein the system is sized, shaped and adapted for dispensing drug in the gastrointestinal tract.

6. The osmotic therapeutic system for dispensing drug according to claim 1, wherein the system is sized, shaped and adapted for vaginal use.

7. The osmotic therapeutic system for dispensing drug according to claim 1, wherein the system is sized, shaped and adapted to be placed in the anus.

8. The osmotic therapeutic system for dispensing a drug according to claim 1, wherein the lamina that forms the microporous lamina is thicker than the semipermeable lamina and which formed microporous lamina provides structural support for said semipermeable lamina.

9. The osmotic therapeutic system for dispensing drug according to claim 1, wherein the microporous lamina is distant from the compartment and faces the biological environment and is formed in the biological environment, with the formed lamina having a plurality of micropores with paths through the lamina and permeable to the passage of fluid through said paths.

10. The osmotic therapeutic system for dispensing drug according to claim 1, wherein the system is sized, shaped and adapted for oral administration and the drug is a member selected from the group consisting of locally and systemically acting drugs.

11. The osmotic therapeutic system for the controlled dispensing of a beneficial drug according to claim 1, wherein the semipermeable lamina contains a flux regulator selected from the group consisting of aliphatic diols, polyalkylene glycols, poly($\alpha,\omega$)alkylenediols, esters of alkylene glycols and mixtures thereof.

12. The osmotic therapeutic system for the controlled dispensing of beneficial drug according to claim 1, wherein the semipermeable lamina also comprise a stabilizing material possessing different chemical and physical properties than the semipermeable lamina forming material, and which stabilizer material is a member selected from the group consisting of a cellulose ester and a cellulose ether.

13. The osmotic therapeutic system for the controlled dispensing of a beneficial drug according to claim 1, wherein the semipermeable lamina also comprises a cyclic or acyclic plasticizer selected from the group consisting of phthalates, phosphates, citrates, adipates, tartrates, sebacates, succinates, glycolates, glycerolates, benzoates, myristates, sulfonamides and halogenated phenyls.

14. The osmotic therapeutic system for dispensing drug according to claim 1, wherein the microporous lamina is formed in the biological environment by leaching from the lamina a a soluble component, which component is soluble in water and biological fluid, and the micropores thus formed by leaching the component have a radius of $$r = \left( 8\eta \frac{J \cdot \Delta x \cdot \tau}{\Delta P \cdot \epsilon} \right)^{\frac{1}{2}}$$

wherein J is the volume flux per unit area, $\eta$ is the viscosity of the liquid, $\epsilon$ is the porosity, $\Delta P$ is the pressure difference across the lamina, $\Delta x$ is the thickness of the lamina and $\tau$ is the tortuosity.

* * * * *